(12) United States Patent
Carlyle et al.

(10) Patent No.: US 10,517,704 B2
(45) Date of Patent: Dec. 31, 2019

(54) DENTAL TREATMENT APPLIANCE

(71) Applicant: Dyson Technology Limited, Wiltshire (GB)

(72) Inventors: Thomas Alexander Carlyle, Swindon (GB); Peter Joel Davies, Swindon (GB)

(73) Assignee: Dyson Technology Limited, Malmesbury, Wiltshire (GB)

(*) Notice: Subject to any disclaimer, the term of this patent is extended or adjusted under 35 U.S.C. 154(b) by 0 days.

(21) Appl. No.: 15/886,280

(22) Filed: Feb. 1, 2018

(65) Prior Publication Data

US 2018/0221124 A1    Aug. 9, 2018

(30) Foreign Application Priority Data

Feb. 3, 2017   (GB) .................................. 1701805.2

(51) Int. Cl.
*A46B 11/04* (2006.01)
*A61C 17/02* (2006.01)
(Continued)

(52) U.S. Cl.
CPC ............ *A61C 17/0202* (2013.01); *A46B 9/04* (2013.01); *A46B 11/002* (2013.01); *A46B 11/066* (2013.01); *A61C 17/34* (2013.01); *A46B 13/04* (2013.01); *A46B 2200/1066* (2013.01); *A61C 17/227* (2013.01)

(58) Field of Classification Search
CPC ... A61C 17/02; A61C 17/0202; A61C 17/221; A61C 17/227; A61C 17/3472; A61C 17/36; A61C 17/3436; A61C 17/3445; A61C 17/3554; A46B 11/002; A46B 11/066; A46B 2200/1066
See application file for complete search history.

(56) References Cited

U.S. PATENT DOCUMENTS 3,424,156 A   1/1969   Smith
5,393,228 A   2/1995   Policicchio
(Continued)

FOREIGN PATENT DOCUMENTS

DE   10 2005 014 095   10/2006
FR      2 789 887       8/2000
(Continued)

OTHER PUBLICATIONS

International Search Report and Written Opinion dated Mar. 13, 2018, directed to International Application No. PCT/GB2018/050009; 10 pages.

(Continued)

*Primary Examiner* — Jennifer C Chiang
(74) *Attorney, Agent, or Firm* — Morrison & Foerster LLP

(57) ABSTRACT

A dental treatment appliance includes a handle, a nozzle for engaging the teeth of the user and for delivering a burst of working fluid to the teeth of a user, and a datum component also for engaging the teeth of the user. Each of the nozzle and the datum component is moveable relative to the handle. A control circuit detects relative movement between the nozzle and the datum component as the appliance is moved along the teeth of a user, and actuates the delivery of working fluid to the teeth of the user depending on the detected relative movement.

30 Claims, 21 Drawing Sheets

(51) Int. Cl.
- *A46B 9/04* (2006.01)
- *A46B 11/00* (2006.01)
- *A46B 11/06* (2006.01)
- *A61C 17/34* (2006.01)
- *A46B 13/04* (2006.01)
- *A61C 17/22* (2006.01)

(56) References Cited

U.S. PATENT DOCUMENTS

| | | |
|---|---|---|
| 6,766,549 B2 * | 7/2004 | Klupt .................... A61C 17/28 |
| | | 15/22.1 |
| 8,522,384 B2 | 9/2013 | Leung |
| 10,034,730 B2 * | 7/2018 | Skaanland ......... A46B 15/0012 |
| 10,034,731 B2 * | 7/2018 | Chang ................ A61C 17/0202 |
| 2001/0012605 A1 | 8/2001 | Kawamura |
| 2002/0152565 A1 | 10/2002 | Klupt |
| 2005/0271531 A1 | 12/2005 | Brown, Jr. et al. |
| 2006/0078844 A1 | 4/2006 | Goldman et al. |
| 2009/0251687 A1 | 10/2009 | Duineveld et al. |
| 2010/0216090 A1 | 8/2010 | Kotlarchik et al. |
| 2011/0000502 A1 | 1/2011 | Eubank |
| 2011/0091837 A1 | 4/2011 | Zolhayat |
| 2011/0143310 A1 | 6/2011 | Hunter |
| 2012/0160263 A1 | 6/2012 | Kotlarchik et al. |
| 2012/0189976 A1 | 7/2012 | McDonough et al. |
| 2012/0266396 A1 | 10/2012 | Leung |
| 2013/0247321 A1 | 9/2013 | Sichau |
| 2015/0202030 A1 | 7/2015 | Miller |
| 2015/0257862 A1 | 9/2015 | Dishon |
| 2015/0374454 A1 | 12/2015 | Beerstecher et al. |
| 2016/0015492 A1 | 1/2016 | Skaanland |
| 2016/0192769 A1 | 7/2016 | Bloch |
| 2016/0310248 A1 | 10/2016 | Meerbeek et al. |
| 2016/0317267 A1 | 11/2016 | Meerbeek et al. |
| 2016/0331117 A1 | 11/2016 | Follows et al. |
| 2018/0125621 A1 | 5/2018 | Tweedie et al. |
| 2018/0125624 A1 | 5/2018 | Tweedie |
| 2018/0177489 A1 | 6/2018 | Yu et al. |
| 2018/0289458 A1 | 10/2018 | Follows et al. |

FOREIGN PATENT DOCUMENTS

| | | |
|---|---|---|
| GB | 2098468 | 11/1982 |
| GB | 2538299 | 11/2016 |
| GB | 2538308 | 11/2016 |
| GB | 2538309 | 11/2016 |
| JP | 55-92312 | 6/1980 |
| JP | 56-150435 | 11/1981 |
| JP | 58-15855 | 1/1983 |
| JP | 7-222757 | 8/1995 |
| JP | 11-128252 | 5/1999 |
| JP | 2001-513358 | 9/2001 |
| JP | 2004-97776 | 4/2004 |
| JP | 2008-501412 A | 1/2008 |
| JP | 2010-526638 | 8/2010 |
| JP | 2013-226202 | 11/2013 |
| JP | 2014-205144 | 10/2014 |
| JP | 2015-530145 | 10/2015 |
| JP | 2016-501618 | 1/2016 |
| JP | 2016-508811 | 3/2016 |
| JP | 2016-539721 | 12/2016 |
| RU | 2463016 | 10/2012 |
| WO | 99/07305 | 2/1999 |
| WO | WO-02/11641 | 2/2002 |
| WO | 2004/021958 | 3/2004 |
| WO | WO-2005/076818 | 8/2005 |
| WO | 2007/025244 A2 | 3/2007 |
| WO | 2008/147360 | 12/2008 |
| WO | 2013/095462 | 6/2013 |
| WO | WO-2014/033599 | 3/2014 |
| WO | 2014/140964 A1 | 9/2014 |
| WO | 2015/087176 A1 | 6/2015 |
| WO | 2015/087219 A1 | 6/2015 |
| WO | WO-2015/087219 | 6/2015 |
| WO | WO-2016/185154 | 11/2016 |

OTHER PUBLICATIONS

Search Report dated Apr. 19, 2017, directed to GB Application No. 1701805.2; 2 pages.

Tweedie et al., U.S. Office Action dated Jun. 28, 2019, directed to U.S. Appl. No. 15/802,898; 10 pages.

Tweedie et al., U.S. Office Action dated Feb. 25, 2019, directed to U.S. Appl. No. 15/802,898; 10 pages.

\* cited by examiner

DENTAL TREATMENT APPLIANCE

REFERENCE TO RELATED APPLICATIONS

This application claims the priority of United Kingdom Application No. 1701805.2, filed Feb. 3, 2017, the entire contents of which are incorporated herein by reference.

FIELD OF THE INVENTION

The present invention relates to a dental treatment appliance. In a preferred embodiment, the appliance is an electric toothbrush having a fluid delivery system for delivering a fluid to the teeth of the user. This fluid may be toothpaste, or a fluid for improved interproximal cleaning. Alternatively, the appliance may not include any bristles or other elements for brushing teeth, and may be in the form of a dedicated interproximal treatment appliance. The present invention also relates to a dental treatment appliance for treating the teeth of the user, for example using a fluid, acoustic waves or electromagnetic radiation emitted by the appliance, or by physically dislodging matter from the teeth of the user.

BACKGROUND OF THE INVENTION

Electric toothbrushes generally comprise a tool which is connected to a handle. The tool comprises a stem and a brush head bearing bristles for brushing teeth. The brush head comprises a static section which is connected to the stem, and at least one moveable section which is moveable relative to the static section, for example with one of a reciprocating, oscillating, vibrating, pivoting or rotating motion, to impart a brushing movement to bristles mounted thereon. The stem houses a drive shaft which couples with a transmission unit within the handle. The transmission unit is in turn connected to a motor, which is driven by a battery housed within the handle. The drive shaft and the transmission unit convert rotary or vibratory motion of the motor into the desired movement of the moveable section of the brush head relative to the static section of the brush head.

It is known to incorporate into an electric toothbrush an assembly for generating a jet of fluid for interproximal cleaning. For example, WO2016/185154 describes a toothbrush having a handle and a brush head which includes a nozzle from which a burst of working fluid is delivered to the teeth of the user. The nozzle is moveable relative to the handle as the appliance is moved along the user's teeth. The toothbrush is operable in a selected one of two different modes. In a first mode, the user depresses a button to actuate the delivery of a burst of working fluid from the nozzle. In a second mode, a control circuit actuates the delivery of a burst of working fluid to the nozzle automatically depending on a signal received from a sensor for detecting movement of the nozzle relative to the handle, for example as the nozzle moves into, or out from, an interproximal gap in the user's teeth.

SUMMARY OF THE INVENTION

In a first aspect, the present invention provides a dental treatment appliance comprising a handle; a datum component for engaging the teeth of a user, the datum component being moveable relative to the handle; and a dental treatment system comprising a contact member for engaging the teeth of the user, the contact member also being moveable relative to the handle, and means for actuating the treatment of the teeth of a user depending on relative movement between the contact member and the datum component as the appliance is moved along the teeth of a user.

As the appliance is moved along, for example, a facial surface of a tooth of the user, whilst there may be some movement of the movable member and the datum component relative to the handle due to variations in the shape of the tooth and/or the force with which the appliance is pressed against the surface of the tooth, there will be relatively little, or no, relative movement between the contact member and the datum component. As the appliance moves over an interproximal gap between adjacent teeth, the contact member will enter the interproximal gap. This relatively large movement of the moveable relative to the datum component actuates the treatment of the teeth of the user.

The treatment of the teeth of the user may be in the form of the emission of acoustic waves or electromagnetic radiation from the appliance. In this case, the contact member may comprise an outlet from which acoustic waves or electromagnetic radiation is emitted from the appliance. Alternatively, the treatment of the teeth of the user may involve physically dislodging matter from the teeth of the user. In this case, the contact member may be in the form of a probe or stylus which moves across the teeth of the user, and the dental treatment system may comprise a pick or bristle tuft for dislodging matter from the teeth of the user.

In a preferred embodiment, the dental treatment system comprises a fluid delivery system for delivering a burst of working fluid to the teeth of a user, for example to dislodge matter located within a gap between the user's teeth. The fluid delivery system preferably comprises a nozzle from which the burst of working fluid is emitted from the fluid delivery system, and in a preferred embodiment the nozzle provides the contact member of the dental treatment appliance. However, the nozzle may be spaced from the contact member, which, as mentioned above, may be in the form of a probe or stylus which moves across the teeth of the user. The nozzle is preferably formed from resilient material, such as an elastomeric material or a rubber.

The actuating means preferably comprises a control circuit. The control circuit may be a mechanical control circuit which actuates the treatment of the teeth of the user depending on the extent and/or the direction of the relative movement between the contact member and the datum component. Alternatively, the control circuit may be an electrical control circuit. In a preferred embodiment, the control circuit is configured to detect relative movement between the contact member and the datum component as the appliance is moved along the teeth of a user, and to actuate the treatment of the teeth of the user depending on the detected relative movement.

In a second aspect, the present invention provides a dental treatment appliance comprising a handle; a fluid delivery system comprising a nozzle for engaging the teeth of the user and for delivering a burst of working fluid to the teeth of a user, the nozzle being moveable relative to the handle; a datum component for engaging the teeth of the user, the datum component also being moveable relative to the handle; and a control circuit for detecting relative movement between the nozzle and the datum component as the appliance is moved along the teeth of a user, and for actuating the delivery of working fluid to the teeth of the user depending on the detected relative movement.

The appliance preferably comprises a head, and a stem extending between the head and the handle. The head preferably comprises both the datum component and the contact member. The datum component and the contact member preferably protrude outwardly from a common side or face of the head.

The datum component is preferably located adjacent to, or alongside, the contact member. The datum component may be located between the contact member and the handle. Alternatively, the contact member may be located between the datum component and the handle. Preferably, the datum component extends at least partially about the contact member. In a preferred embodiment, the datum component surrounds the contact member.

The contact member and the datum component are preferably moveable relative to the handle in substantially the same direction.

At least part of each of the contact member and the datum component is preferably biased for movement relative to the handle in a direction which urges it against a user's teeth during use of the appliance. The contact member preferably comprises a tip portion for engaging the user's teeth. In a preferred embodiment, the tip portion comprises a fluid outlet from which a burst of working fluid is ejected towards the teeth of a user. The appliance preferably comprises a resilient element for biasing the contact member for movement relative to the handle in such a direction that the contact member is urged against a user's teeth during use of the appliance. The resilient member preferably exerts a force on the contact member which is of a sufficient magnitude to allow the contact member to move, against the biasing force of the resilient member, as it is pressed against the user's teeth, and without exerting an excessive force on the teeth which is uncomfortable for the user. This resilient element may comprise a spring for engaging the contact member, or a component connected to the contact member, to bias the contact member for movement in this direction. Alternatively, the contact member may be biased in this direction by part of the treatment system, for example a resilient fluid conduit of a fluid delivery system. The contact member is preferably moveable between a distal position and a proximal position relative to the head. The contact member is preferably biased for movement towards the distal position.

In a preferred example, the contact member is moveable relative to the handle about an axis. This axis is preferably substantially orthogonal to the longitudinal axis of the handle. The axis is preferably angled to a longitudinal axis of the contact member, and is more preferably substantially orthogonal to the longitudinal axis of the contact member. The appliance preferably comprises a contact member support which is connected to the contact member, and which is moveable relative to the handle. For example, the contact member support may be pivotably connected to the handle, or to a stem extending between the head and the handle, for movement about a pivot axis. Where the treatment system comprises a fluid delivery system, the contact member support may be connected directly to the resilient fluid conduit, directly to a relatively rigid fluid conduit of the fluid delivery system which moves with that resilient fluid conduit, or connected between those fluid conduits.

The datum component preferably comprises at least one datum surface for engaging a user's teeth during use of the appliance. The datum component may comprise a single, substantially planar, datum surface. This datum surface may be annular in shape, and may extend about a longitudinal axis of the nozzle, hereafter referred to as the nozzle axis. The datum surface may be formed from plastics material. Alternatively, the datum component may comprise a plurality of datum surfaces. These datum surfaces may be arranged about the contact member. The datum surfaces are preferably substantially coplanar. The datum surfaces may be arranged regularly or irregularly about the contact member. The datum surfaces may have similar or various different surface areas. The datum surfaces may be disposed on a single body extending about the contact member. Alternatively, each datum surface may be provided by the tip of a respective body or finger of the datum component. These fingers are preferably arranged about the contact member. The fingers of the datum component may be provided by a plurality of bristles or bristle tufts arranged about the contact member. Alternatively, the fingers may be provided by a plurality of resilient or elastomeric members arranged about the contact member. These elastomeric members may be arranged radially or circumferentially about the contact member. The elastomeric members may be regularly angularly spaced about the contact member.

The appliance preferably comprises a resilient member for biasing the datum component in said direction to urge the datum surface(s) against a user's teeth during use of the appliance. Again, the resilient member preferably exerts a force on the datum component which is of a sufficient magnitude to allow the datum component to move, against the biasing force of the resilient member, as it is pressed against the user's teeth, and without exerting an excessive force on the teeth which is uncomfortable for the user. The resilient member may comprise a spring for engaging the datum component, or another component connected to the datum component, to bias the datum component for movement in this direction. Alternatively, a resilient portion of the datum component may urge the datum surface to move in this direction. For example, the datum component may comprise a resilient portion of the body of the datum component, such as a bellows, which is located between the datum surface and a stationary member which is connected to the handle.

The datum component preferably comprises a sleeve which surrounds the nozzle. The bellows is preferably connected to, and extends about, the sleeve. The contact member preferably comprises a flange for engaging an inner surface of the sleeve to form a seal therewith to inhibit the ingress of fluid or other debris into the head of the appliance from between the contact member and the datum component.

The datum component is also preferably moveable between a distal position and a proximal position relative to the head. The datum component is preferably biased for movement towards the distal position. When each of the contact member and the datum component is in its distal position, the tip of the contact member is preferably substantially coplanar with the datum surface(s) of the datum component.

In a preferred example, the datum component is moveable relative to the handle about an axis. This axis is preferably substantially orthogonal to the longitudinal axis of the handle. The axis is preferably collinear with the axis about which the contact member is moveable relative to the handle. The appliance preferably comprises a datum component support which is connected to the datum component, and which is moveable relative to the handle. For example, the datum component support may be pivotably connected to the handle, or to the stem extending between the head and the handle, for movement about the pivot axis. The datum component support may be connected directly to the datum component, or to an arm extending between the datum component support and the datum component. The arm is preferably connected to the sleeve of the datum component.

The arm is preferably biased for movement about the pivot axis by the resilient portion of the contact member.

As measured in the direction of the longitudinal axis of the handle, the width of the datum component is preferably greater than the width of the contact member. The contact member is preferably shaped such that at least a tip portion of the contact member can move into, and out from, a typical interproximal gap as the appliance is moved along the teeth of the user. The width or diameter of the tip of the contact member is preferably in the range from 0.5 to 1.5 mm, and in a preferred embodiment is around 1 mm. On the other hand, the datum component is preferably shaped such that the datum component does not move into a typical interproximal gap as the appliance is moved along the teeth of the user, but instead provides a bridge between the teeth on either side of the gap. The width of the tooth engaging region of the datum component, which may be defined by a single datum surface or a plurality of datum surfaces, is preferably in the range from 5 to 10 mm, and in a preferred embodiment is around 7 mm.

As mentioned above, the control circuit is arranged to detect relative movement between the contact member and the datum component as the appliance is moved along the teeth of a user, and to actuate the treatment of the teeth of the user depending on the detected relative movement. The control circuit preferably comprises at least one sensor. The control circuit preferably comprises a controller for receiving signals output from the sensor(s), and for actuating the treatment of the teeth of the user.

In one embodiment, the control circuit comprises a sensor for providing an output which varies with relative movement between the contact member and the datum component, and a controller for actuating the treatment of the teeth of the user depending on the output from the sensor. The sensor may be located at a convenient location within the appliance for detecting the relative movement between the contact member and the datum component. For example, the sensor may be located in the head. Alternatively, the sensor may be located in the handle of the appliance to facilitate its connection to a controller located in the handle of the appliance. Where the sensor is located in the head, the appliance may comprise one or more conductors, such as cables or flexes, for connecting the sensor to the controller.

The sensor may be located within the head of the appliance. The sensor may be mounted on a stationary component of the appliance, that is, a component relative to which each of the contact member and the datum component is moveable. Alternatively, the sensor may be connected to, or mounted on, one of the contact member and the datum component, and arranged to detect movement of the other one of the contact member and the datum component relative thereto. The sensor may be in the form of a motion detector. For example, the sensor may be in the form of a light detector, such a camera or a light sensor, for receiving light reflected from the other one of the contact member and the datum component. Alternatively, the appliance may comprise a component connected to, or mounted on, the other one of the contact member and the datum component, and the sensor may be arranged to provide an output which varies with movement of the component relative thereto. This component may be reflective, or formed from magnetic material, with the sensor being arranged to detect the movement of that magnetic component from the variation in the magnetic field experienced by the sensor. For example, the sensor may be a Hall effect sensor.

Alternatively, the sensor may be located remotely from the head of the appliance. For example, the sensor may be located in the stem or in the handle. The sensor may be arranged to detect movement of a component, such as a magnet, which is connected to the contact member and the datum component via a linkage mechanism.

The linkage mechanism may be arranged to convert a relative movement between the contact member and the datum component into a movement of the magnet relative to the sensor. For example, the linkage mechanism may comprise a four bar linkage, in which two input links are connected to the contact member and the datum component respectively for movement about the common pivot axis, and two output links, each pivotably connected to a respective one of the input links, are connected to a slider which is moveable within a curved slot or track connected to the magnet. Movement of the contact member with the datum component causes the slider to move along the track while the track remains stationary, whereas relative movement between the contact member and the datum component causes the track, and the magnet connected thereto, to move with the slider relative to the handle.

Alternatively, the linkage mechanism may be arranged to convert movement of the contact member relative to the handle into a movement of the magnet along a first axis, and to convert movement of the datum component relative to the handle into a movement of the magnet along a second axis which is orthogonal to the first axis. In this case, the controller is configured to detect relative movement between the contact member and the datum component from the output of the sensor, and to actuate the treatment of the teeth of the user depending on the detected relative movement.

In another embodiment, the control circuit comprises a first sensor for providing an output which varies with movement of the contact member relative to the handle, a second sensor for providing an output which varies with movement of the datum component relative to the handle, and a controller for detecting relative movement between the contact member and the datum component from the outputs of the sensors, and for actuating the treatment of the teeth of the user depending on the detected relative movement.

The sensors may be located at convenient locations within the appliance for detecting the movements of the contact member and the datum component relative to the handle. For example, each sensor may be located within the head of the appliance. Each sensor may be mounted on a stationary component of the appliance, that is, a component relative to which each of the contact member and the datum component is moveable. Each sensor may be in the form of a motion detector. For example, each sensor may be in the form of a light detector, such a camera or a light sensor, for receiving light reflected from the contact member and the datum component respectively. Alternatively, the appliance may comprise a first component connected to, or mounted on, the contact member for movement therewith, and wherein the first sensor is arranged to provide an output which varies with movement of the first component relative to the handle, and a second component connected to, or mounted, the datum component for movement therewith, and wherein the second sensor is arranged to provide an output which varies with movement of the second component relative to the handle. The first component preferably comprises a first magnet, and the second component preferably comprises a second magnet. The first sensor is preferably arranged to generate an output which varies depending on the relative positions between the first sensor and the first magnet, and the second sensor is preferably arranged to generate an output which varies depending on the relative positions between the second sensor and the second magnet. Each of the first sensor and the second sensor is preferably a Hall effect sensor.

Alternatively, the sensors may be located remotely from the head of the appliance. For example, each sensor may be located in the stem or in the handle. Each sensor may be arranged to detect movement of a respective magnet which is connected to a respective one of the contact member and the datum component. For example, the first magnet may be connected to a first arm which is connected to the contact member support for movement therewith about the common pivot axis, and the second magnet may be connected to a second arm which is connected to the datum component support for movement therewith about the pivot axis.

Depending on the detected relative movement, the controller is arranged to actuate the treatment of the teeth of the user, which in a preferred embodiment comprises a delivery of working fluid to the teeth of the user. The fluid delivery system preferably comprises a pump, and the controller is preferably arranged to actuate the pump to eject a burst of working fluid towards the nozzle. The volume of each burst of working fluid which is generated by the fluid delivery system is preferably less than 1 ml, more preferably less than 0.5 ml. In a preferred embodiment, the volume of the burst of working fluid generated by the fluid delivery system is in the range from 0.1 to 0.4 ml, and is preferably around 0.25 ml. The fluid delivery system is preferably configured to deliver a burst of working fluid to the nozzle at a static pressure in the range from 3 to 10 bar.

The pump is preferably a positive displacement pump, such as a piston pump or a diaphragm pump. A hydraulic accumulator may be provided between the pump and the nozzle for storing working fluid at a pressure in the range from 3 to 10 bar. In this case, the fluid delivery system may comprise a valve, such as a solenoid valve, located downstream from the accumulator, and the controller may be configured to change the position of the valve from a closed position to an open position to release working fluid from the accumulator.

The appliance may be in the form of a dedicated interproximal treatment appliance for cleaning between the gaps in the user's teeth. Alternatively, the appliance may be in the form of a toothbrush which has the additional function of improved interproximal cleaning, for example through the emission of a burst of working fluid into the interproximal gap. Where the appliance is in the form of a toothbrush, the appliance preferably comprises a plurality of bristles. The bristles are preferably arranged around, and preferably circumferentially about, the contact member and the datum component.

The plurality of bristles may be attached to a static section of the head, which section is not moveable relative to the handle. Alternatively, or additionally, a plurality of bristles may be attached to a moveable section of the head, which section is moveable relative to the handle, the contact member and the datum component. In a preferred embodiment, the appliance comprises a brush unit comprising a bristle carrier and a plurality of bristles mounted on the bristle carrier, with the bristle carrier being moveable relative to the handle. The contact member and the datum component are each preferably biased for movement relative to the brush unit in a direction extending away from the brush unit.

In addition to the movement of the contact member and the datum component relative to the brush unit, the brush unit is preferably moveable relative to the contact member and the datum component. The movement of the brush unit, to enable the ends of the bristles to be swept over the surfaces of the teeth of the user, may thus be independent from the movements of the contact member and the datum component relative to the handle. The bristle carrier may translate, rotate, pivot or vibrate relative to the head. The movement of the bristle carrier relative to the head is preferably about an axis which is substantially parallel to, or collinear with, the longitudinal axis of the handle, and thus preferably substantially perpendicular to the pivot axis of the contact member and the datum component. Alternatively, the handle may comprise a motor for vibrating the bristle carrier, for example through the transmission of vibrations thereto via the stem of the appliance.

The working fluid is preferably a liquid working fluid, and is preferably water. The appliance preferably comprises a fluid reservoir for storing working fluid, and from which working fluid is supplied to the fluid delivery system. The handle of the appliance may comprise the fluid reservoir. For example, the fluid reservoir may be fully contained within a body of the handle. Alternatively, an external wall of the handle may at least partially delimit the fluid reservoir. At least part of that external wall may be transparent to allow a user to see the volume of working fluid contained within the fluid reservoir. Alternatively, the fluid reservoir may be housed within the stem. As above, an external wall of the stem may at least partially delimit the fluid reservoir, and at least part of that external wall may be transparent to allow a user to see the volume of working fluid contained within the fluid reservoir. As an alternative to housing the fluid reservoir within the stem, the fluid reservoir may be connected to the stem so as to be located externally of the stem. This can allow the fluid reservoir to be detached from the stem for replenishment or replacement as required. Alternatively, the fluid reservoir may be partially delimited by an external wall which is connected to the stem. Again, at least part of that external wall may be transparent to allow a user to see the volume of working fluid contained within the fluid reservoir. To maximize the capacity of the fluid reservoir and to provide for a relatively even weight distribution about the longitudinal axis of the appliance, the fluid reservoir preferably extends about, or surrounds, the stem.

The head and the stem preferably form part of a tool which is detachably connected to the handle. This can allow a handle to be provided with a set of similar tools, each with a respective different identifier for use by a different user. This can also allow a handle to be provided with a set of dissimilar tools. For example, the set of tools may be selected from two or more of a first type of tool with a nozzle and a moveable brush unit, a second type of tool with a nozzle and a static brush unit, a third type of tool with a nozzle and no bristles, and a fourth type of tool with a moveable brush unit and no nozzle. A number of respective different tools of the same type may also be provided, for example, of the first type of tool, with bristles having a respective different stiffness, or with nozzles having respective different fluid outlet sizes.

The appliance is preferably a handheld appliance which includes all of the aforementioned components of the appliance.

Features described above in connection with the first aspect of the invention are equally applicable to the second aspect of the invention, and vice versa.

BRIEF DESCRIPTION OF THE DRAWINGS

Preferred features of the present invention will now be described by way of example only with reference to the accompanying drawings, in which.

DETAILED DESCRIPTION OF THE INVENTION

Figure 1:
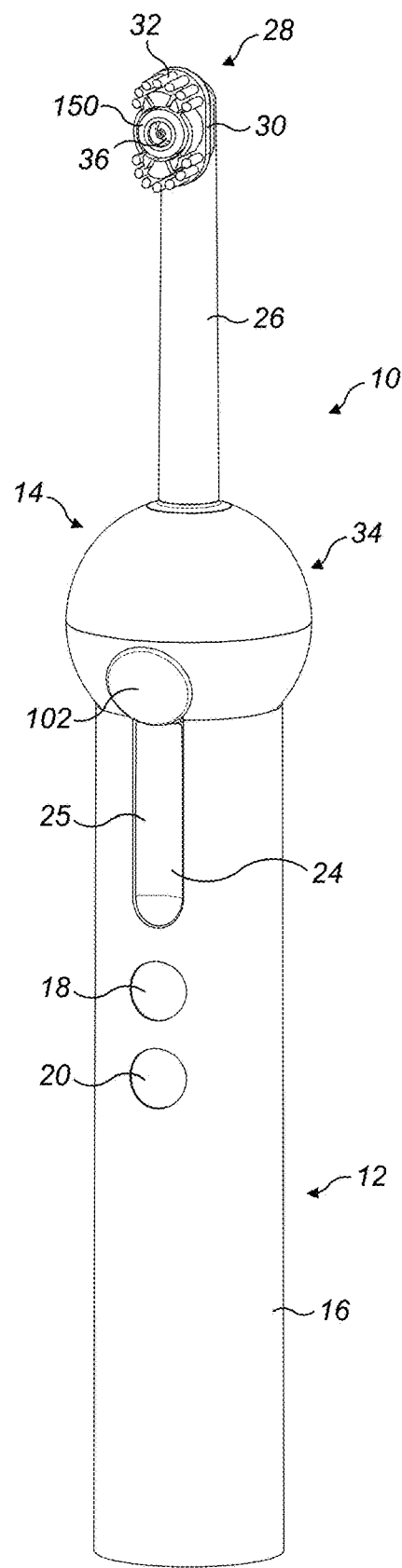
FIG. 1 is a left side perspective view of a first embodiment of a dental treatment appliance.
Figure 2A:
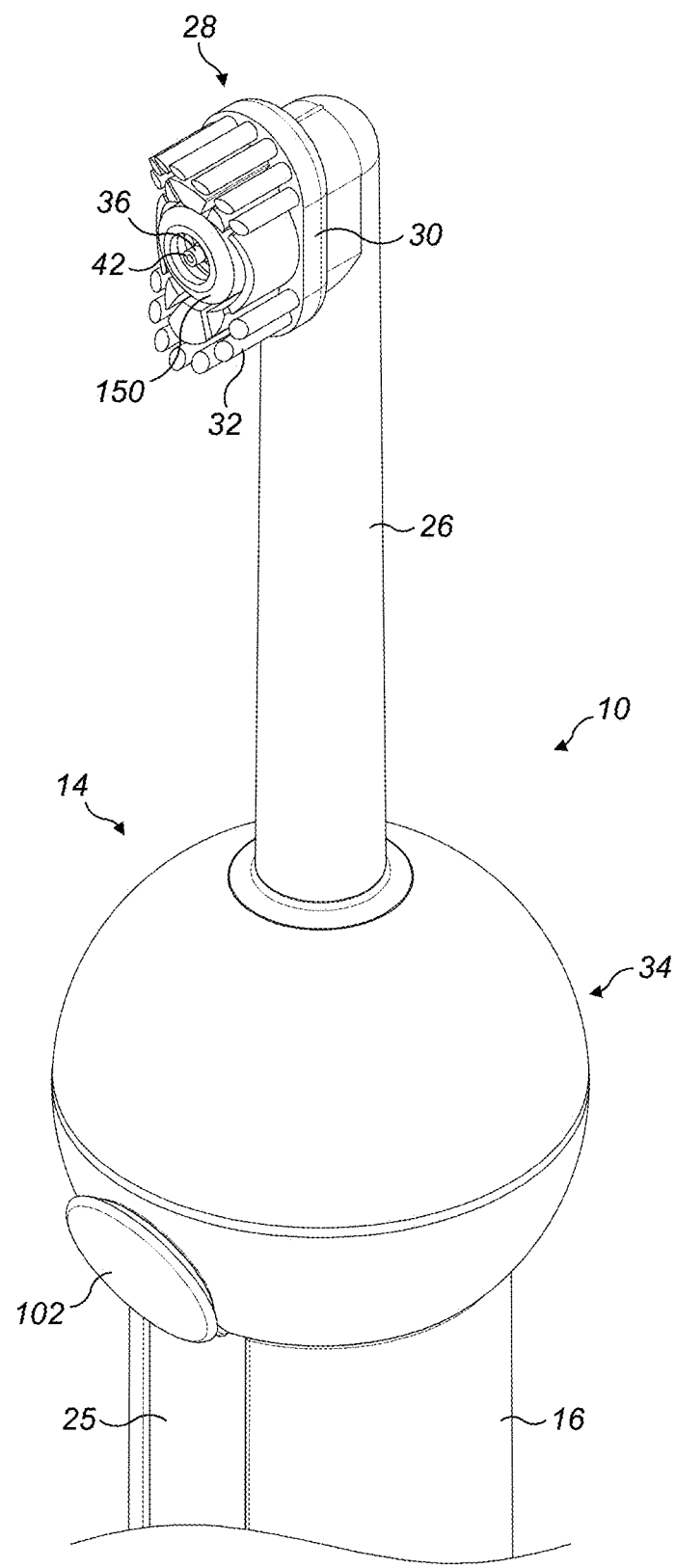
FIG. 2(a) is a left side perspective view of a tool of the appliance.
Figure 2B:
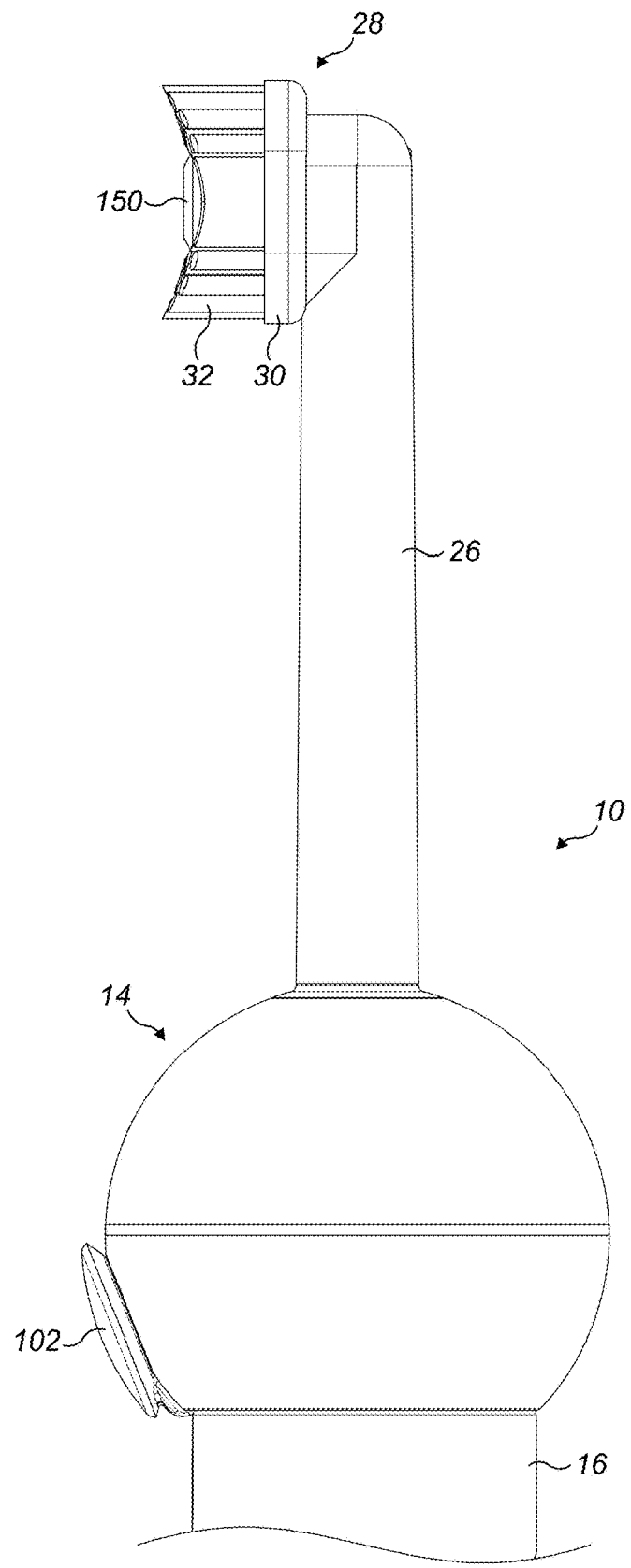
FIG. 2(b) is a left side view of the tool.
Figure 2C:
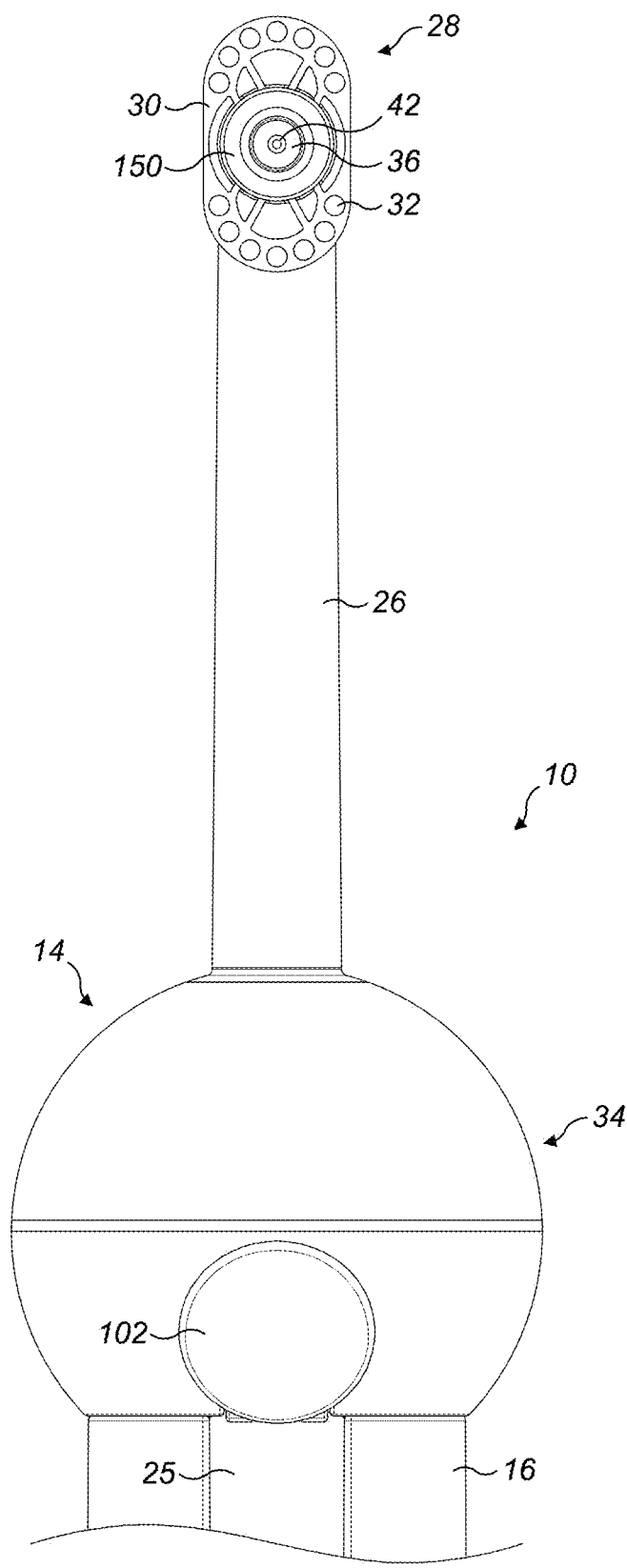
FIG. 2(c) is a front view of the tool.

FIGS. 1 and 2(a) to 2(c) illustrate external views of an embodiment of a dental treatment appliance 10. In this embodiment, the appliance is in the form of a handheld appliance, which is in the form of an electric toothbrush having an integrated assembly for treating the teeth of the user, in this embodiment by dispensing a working fluid for improved interproximal cleaning.

The appliance 10 comprises a handle 12 and a tool 14. The handle 12 comprises a body 16 which is gripped by a user during use of the appliance 10. The body 16 is preferably formed from plastics material, and is preferably generally cylindrical in shape. The handle 12 comprises a plurality of user operable buttons 18, 20, 22 which are located within respective apertures formed in the body 16 so as to be accessible to the user. Buttons 18, 20 are located towards the front of the handle 12, whereas button 22 is located towards the rear of the handle 12 and so is not visible in FIG. 1. The handle 12 may also comprise a display 24 which is positioned so as to be visible to a user during use of the appliance. For example, the display 24 may be visible to the user through the body 16 of the handle 12, or through a transparent panel 25 connected to the body 16 of the handle 12. In this embodiment, the panel 25 is concave in shape.

The tool 14 is preferably detachably connected to the handle 12. The tool 14 comprises a stem 26 and a head 28. The stem 26 is elongate in shape, which serves to space the head 28 from the handle 12 to facilitate user operability of the appliance 10. In this embodiment, the head 28 of the tool 14 comprises a brush unit, which comprises a bristle carrier 30 and a plurality of bristles 32 mounted on the bristle carrier 30. However, in other embodiments the tool 14 may be provided without a brush unit so that the appliance is in the form of a dedicated interproximal treatment appliance for treatment or cleaning between the gaps in the user's teeth.

The tool 14 also comprises a fluid reservoir 34 for storing a working fluid, and a nozzle 36 for delivering one or more bursts of working fluid to the teeth of the user during use of the appliance 10. The fluid reservoir 34 is connected to the stem 26, and preferably extends at least partially around the stem 26. In this embodiment which includes a brush unit, the brush unit extends at least partially around the nozzle 36.

Figure 3:
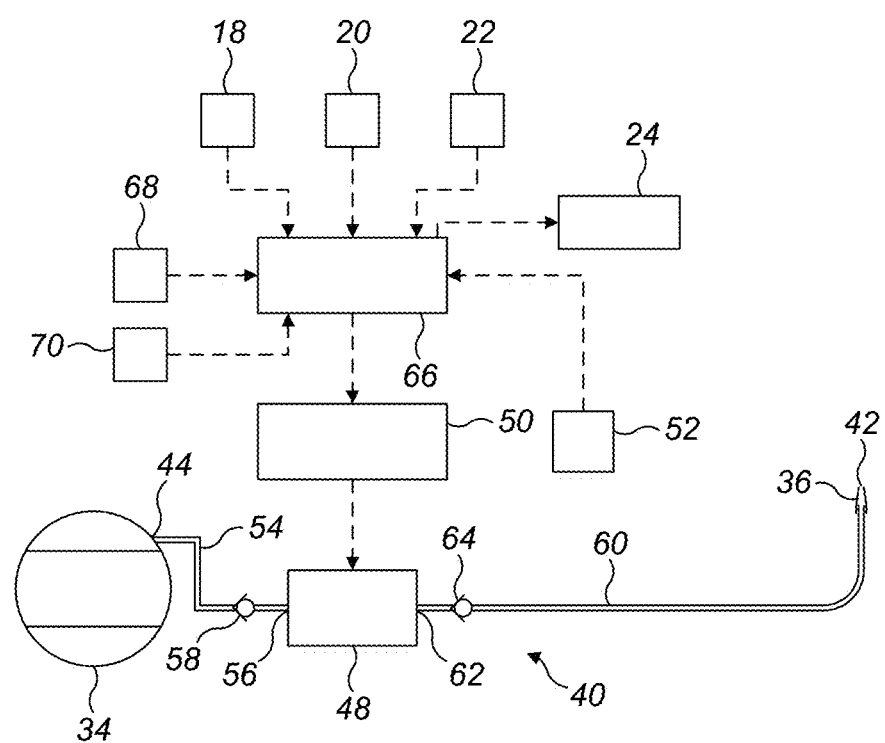
FIG. 3 illustrates schematically components of a fluid delivery system of the appliance.

The nozzle 36 forms part of a dental treatment system of the appliance 10, which in this embodiment comprises a fluid delivery system 40 for receiving working fluid from the fluid reservoir 34 and for delivering bursts of working fluid to the teeth of a user during use of the appliance 10. Each burst of working fluid preferably has a volume which is less than 1 ml, more preferably less than 0.5 ml, and in this example is around 0.25 ml. The tip of the nozzle 36 comprises a fluid outlet 42 through which a burst of working fluid is delivered to the teeth of the user. The fluid delivery system 40 is illustrated schematically in FIG. 3. In overview, the fluid delivery system 40 comprises a fluid inlet 44 for receiving working fluid from the fluid reservoir 34. In this embodiment, the working fluid is a liquid working fluid, which is preferably water. The fluid delivery system 40 comprises a pump assembly for drawing working fluid from the fluid reservoir 34 through the fluid inlet 44, and for delivering a burst of working fluid to the nozzle 36. The pump assembly is located within the handle 12, and comprises a positive displacement pump 48 and a drive for driving the pump 48. The drive preferably comprises a motor 50. A battery 52 for supplying power to the motor 50 is also located in the handle 12. The battery 52 is preferably a rechargeable battery.

A first conduit 54 connects the fluid inlet 44 of the fluid delivery system 40 to a fluid inlet 56 of the pump 48. A first one-way valve 58 is located between the fluid inlet 44 and the pump 48 to prevent water from returning to the fluid reservoir 34 from the pump 48. A second conduit 60 connects a fluid outlet 62 of the pump 48 to the nozzle 36. A second one-way valve 64 is located between the pump 48 and the nozzle 36 to prevent water from returning to the pump 48. A controller 66 of a control circuit controls the actuation of the motor 50, and so the motor 50 and the controller 66 provide a drive for driving the pump 48. The battery 52 supplies power to the controller 66. The controller 66 includes a motor controller, which supplies power to the motor 50.

In this embodiment, the controller 66 receives signals generated when the user depresses the buttons 18, 20, 22 located on the handle 12 of the appliance 10, and drives the display 24. As described in more detail below, the controller 66 also receives signals from sensors 68, 70 of the control circuit. The controller 66 may also receive signals from a remote device, such as a display or a personal device.

The tool 14 is detachably connected to the handle 12. With reference to FIGS. 4(*a*) to 6(*c*), the handle 12 comprises a male connector (not shown), preferably in the form of a spigot, which is received by a complementary female connector, preferably in the form of a recessed connector 72, of the tool 14 housed within, and connected to, a relatively wide base section 74 of the stem 26. The recessed connector 72 defines a generally cylindrical recess 76 for receiving the spigot. The spigot preferably protrudes outwardly from an end surface 78 of the body 16 of the handle 12, and preferably in a direction which is parallel to a longitudinal axis of the handle 12. The end surface 78 defines an annular seat 80 for receiving an annular bottom wall 82 of the fluid reservoir 34 when the tool 14 is mounted on the handle 12. The annular seat 80 comprises the fluid inlet 44 of the fluid delivery system 40. The fluid inlet 44 receives fluid from a reservoir fluid outlet port of the fluid reservoir 34 when the tool 14 is mounted on the handle 12.

The second conduit 60, which connects the fluid outlet 62 of the pump 48 to the nozzle 36, comprises a handle conduit section located within the handle 12, and a tool conduit section 84 located within the tool 14. The handle conduit section extends from the fluid outlet 62 of the pump 48 to a handle fluid outlet port located on the end surface 78 of the body 16 of the handle 12. The tool conduit section 84 comprises a tool fluid inlet port for receiving fluid from the handle fluid outlet port when the tool 14 is connected to the handle 12.

As mentioned above, the tool 14 includes a bristle carrier 30 which is moveable relative to the stem 26. The appliance 10 comprises a drive mechanism for driving the movement of the bristle carrier 30 relative to the stem 26. The drive mechanism comprises a transmission unit connected to the bristle carrier 30, and a drive unit for driving the transmission unit to move the bristle carrier 30 relative to the stem 26.

The handle 12 comprises the drive unit of the drive mechanism. The drive unit comprises a motor, preferably in the form of a dc motor, which is actuated by the controller 66 in response to the user depression of one or more of the buttons of the handle 12. The motor of the drive unit is connected via a gear train to a rotatable drive unit coupling member which protrudes outwardly from the spigot, and which rotates relative to the body 16 upon actuation of the motor of the drive unit. The tool 14 comprises the transmission unit of the drive mechanism. The transmission unit (not shown) comprises a transmission unit coupling member which couples with the drive unit coupling member when the tool 14 is connected to the handle 12. The transmission unit coupling member is connected to, and is preferably integral with, one end of a connecting rod housed within the stem 26 and which is supported for rotation relative to the stem 26 by an annular support 86 mounted on the recessed connector 72. The other end of the connecting rod is connected to the side surface of the bristle carrier 30 so that periodic rotation of the connecting rod about a 15 □ angle results in a 15 □ sweeping movement of the bristle carrier 30 relative to the stem 26.

The fluid reservoir 34 is mounted on, and extends at least partially around, the stem 26 of the tool 14. In this embodiment, the fluid reservoir 34 is annular in shape, and so surrounds the stem 26. The fluid reservoir 34 is preferably located at or towards the end of the stem 26 which is remote from the head 28, and so in this embodiment extends around the base section 74 of the stem 26. The fluid reservoir 34 preferably has a capacity in the range from 5 to 50 ml, and in this embodiment has a capacity of 25 ml.

The fluid reservoir 34 is filled through a reservoir fluid inlet port 100 formed in the external wall of the fluid reservoir 34. The fluid inlet port 100 is preferably formed in an annular external side wall of the fluid reservoir 34. The reservoir fluid inlet port 100 is sealed by a closure member 102. The closure member 102 is moveable relative to the fluid reservoir 34 between a closed position, as shown in FIG. 4(*a*), in which the closure member 102 inhibits the leakage of working fluid from the reservoir fluid inlet port 100, and an open position. In this embodiment, the closure member 102 is pivotably connected to the fluid reservoir 34. The closure member 102 is locatable within, and forms a fluid-tight seal against, the reservoir fluid inlet port 100. The closure member 102 comprises a head 104 which may be gripped by the user to move the closure member 102 from the closed position to the open position, and which may be pushed by the user towards the reservoir fluid inlet port 100 to return the closure member 102 to the closed position.

The closure member 102 is connected to the fluid reservoir 34 by a pair of arms 106. One end of each arm 106 is connected to the closure member 102, and the other end of each arm 106 is connected to the fluid reservoir 34. In this embodiment, the arms 106 are integral with the closure member 102, with a portion of each arm 106 which is remote from the closure member 102 being connected to the bottom wall 82 of the fluid reservoir 34, for example using an adhesive or by welding. Each arm 106 comprises a hinge, which may be formed from a part of the arm 106 which has a locally reduced thickness, to enable the part of the arm 106 which is connected to the closure member 102 to pivot relative to the other part of the arm 106 which is connected to the fluid reservoir 34.

To fill the fluid reservoir 34, the user detaches the tool 14 from the handle 12, grips the head 104 of the closure member 102 between finger and thumb and pulls it out from the reservoir fluid inlet port 100. The fluid reservoir 34 may then be filled by the user, for example by locating the reservoir fluid inlet port 100 beneath a running tap. Once the fluid reservoir 34 has been filled, the user pushes the head 104 of the closure member 102 back into the reservoir fluid inlet port 100, and reconnects the tool 14 to the handle 12.

The external wall of the fluid reservoir 34 preferably has a shape which is symmetrical about the longitudinal axis of the tool 14. The external wall preferably has a curved shape, more preferably a convex curved shape, but alternatively the external wall may have a polygonal or faceted shape. In this embodiment, the external wall has a spherical curvature. In this embodiment, the external wall of the fluid reservoir 34. In this embodiment, the external wall of the fluid reservoir 34 comprises an upper section 108 connected to a lower section 110. The lower section 110 is integral with the bottom wall 82 of the fluid reservoir 34. The upper section 108 of the external wall is preferably formed from transparent material to allow a user to observe the contents of the fluid reservoir 34, and so assess whether the fluid reservoir 34 requires replenishment prior to the desired use of the appliance 10.

The fluid reservoir 34 further comprises an inner wall 112 which is connected to the external wall, and which with the external wall defines the capacity of the fluid reservoir 34. The inner wall 112 is tubular in shape. One end of the inner wall 112 is connected to the internal surface of the upper section 108 of the external wall, whereas the other end of the inner wall is connected to the bottom wall 82.

Figure 4A:
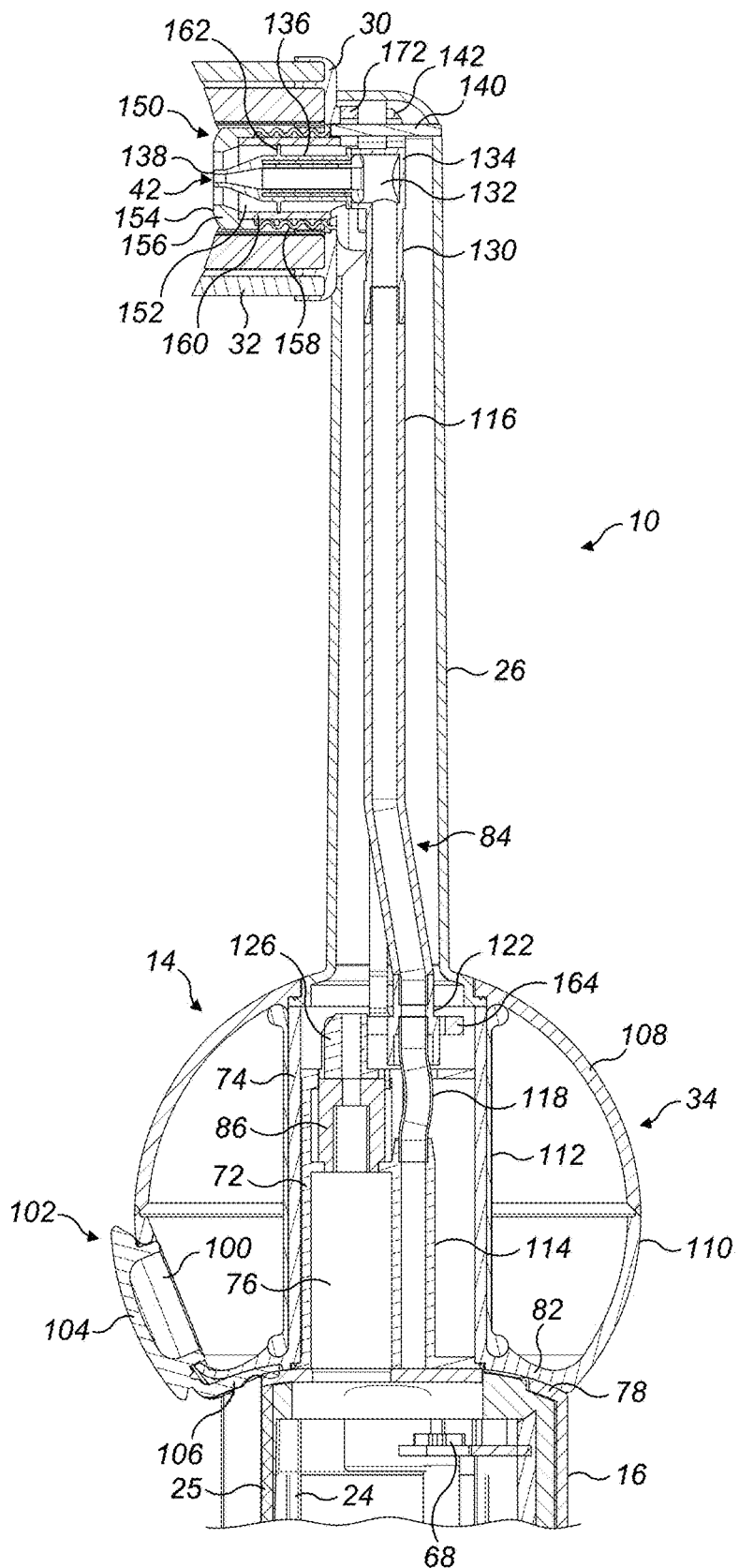
FIG. 4(a) is a side sectional view of the tool, in a first configuration in which both a nozzle and a datum component of the appliance are in a distal position.
Figure 4B:
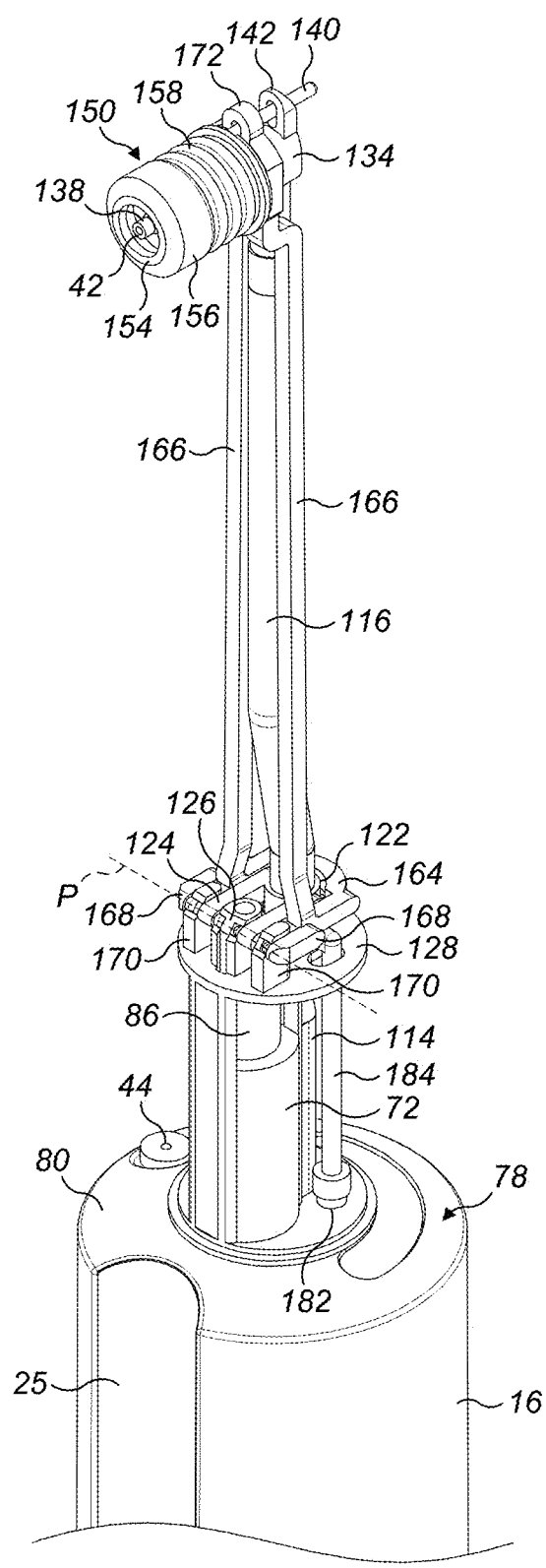
FIG. 4(b) is a perspective view of internal components of the tool when in the first configuration.
Figure 4C:
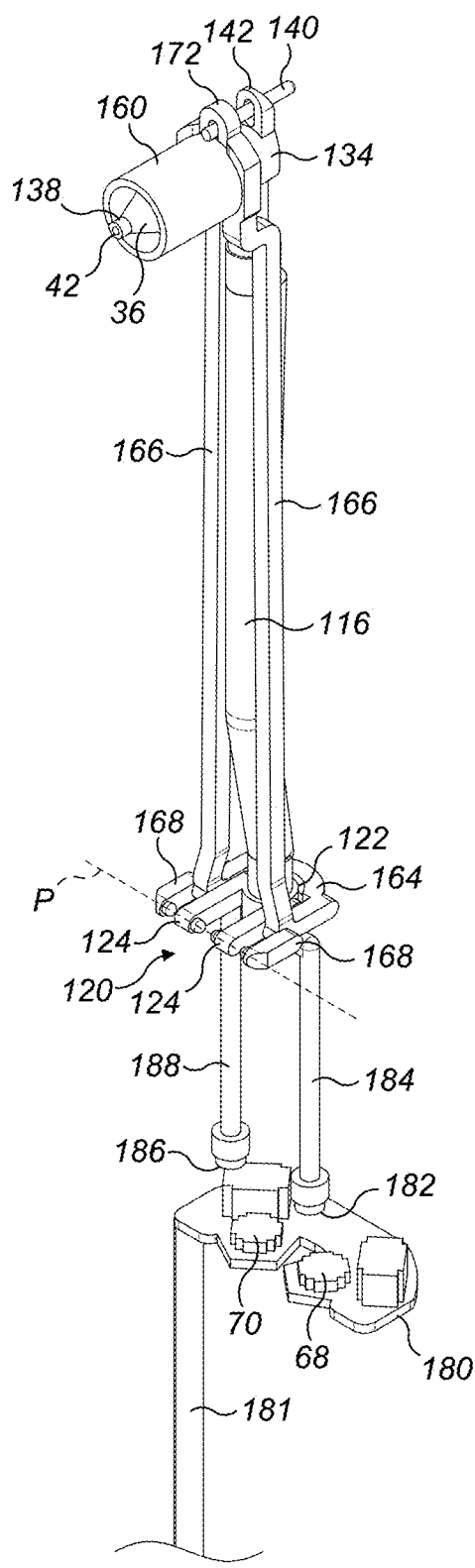
FIG. 4(c) is a perspective view of internal components of both the handle and the tool when in the first configuration.

FIG. 4(b) is a perspective view of the tool 14 mounted on the handle 12, but with the stem 26, fluid reservoir 34 and brush unit removed to reveal components of the tool conduit section 84. FIG. 4(c) is a similar view to FIG. 4(b), but with additional components of the tool 14 and the handle 12 removed. With reference to FIGS. 4(a) to 4(c), the tool conduit section 84 comprises a relatively rigid inlet section 114, which in this embodiment is defined by the recessed connector 72 of the tool 14, for receiving working fluid from the tool fluid inlet port, a relatively rigid outlet section 116 connected to the nozzle 36, and a relatively flexible, resilient section 118 extending between the inlet section 114 and the outlet section 116. The outlet section 116 and the resilient section 118 are supported within the stem 26 by a nozzle support 120. The nozzle support 120 comprises a collar 122 for connecting together the outlet section 116 and resilient section 118 of the tool conduit section 84, and a pair of fingers 124 extending outwardly from the collar 122. The tips of the fingers 124 are pivotably connected to a first bracket 126 mounted on, and preferably integral with, a shelf or platform 128 mounted on the recessed connector 72 to allow the nozzle support 120 to pivot about a pivot axis P. Pivot axis P is substantially orthogonal to the longitudinal axis of the handle 12.

Figure 5A:
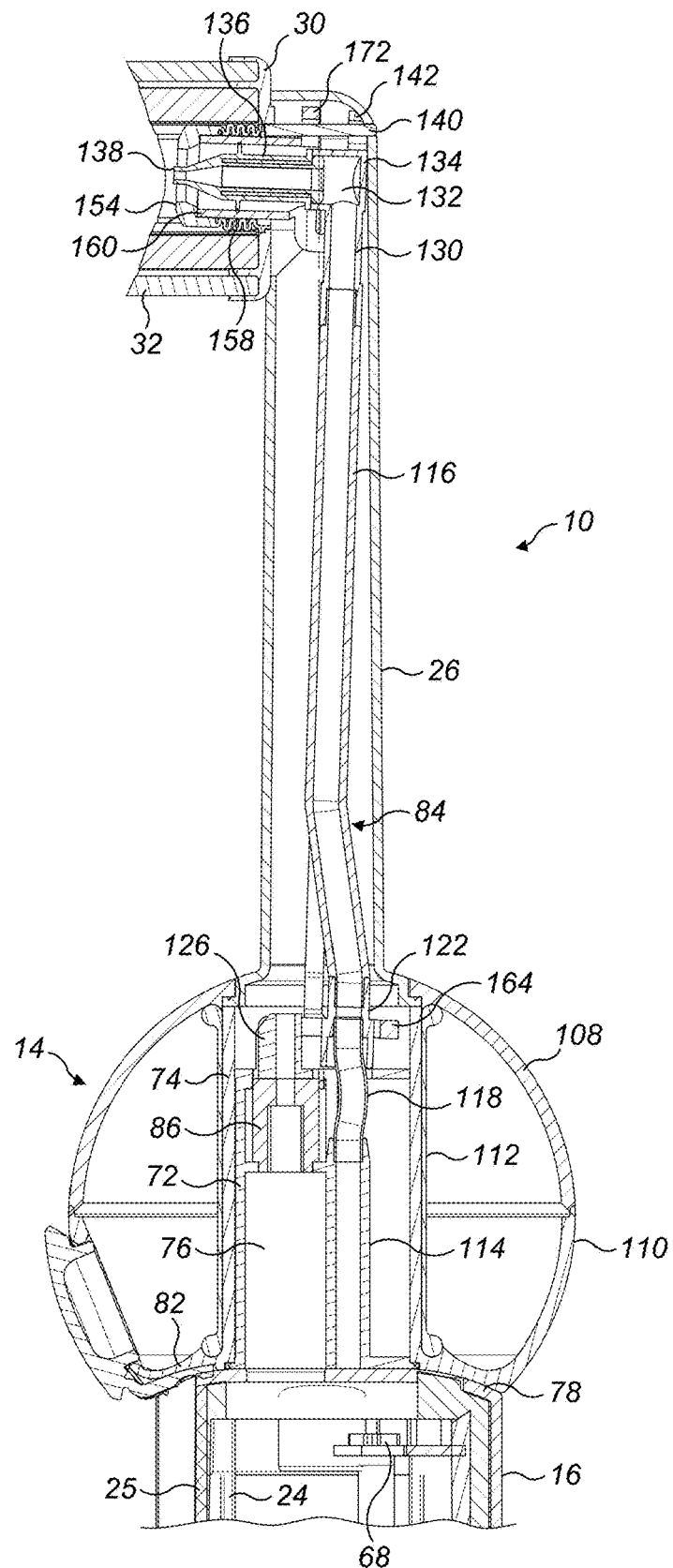
FIG. 5(a) is a side sectional view of the tool, in a second configuration in which both the nozzle and the datum component are in a proximal position.
Figure 5B:
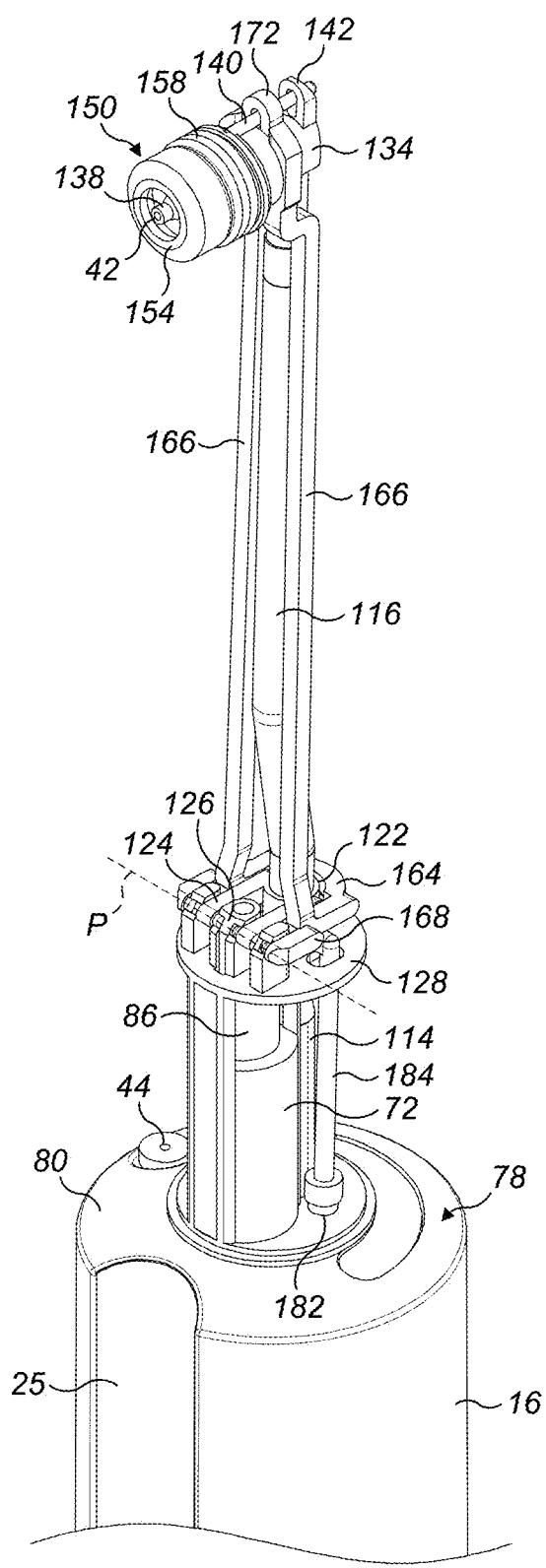
FIG. 5(b) is a perspective view of internal components of the tool when in the second configuration.
Figure 5C:
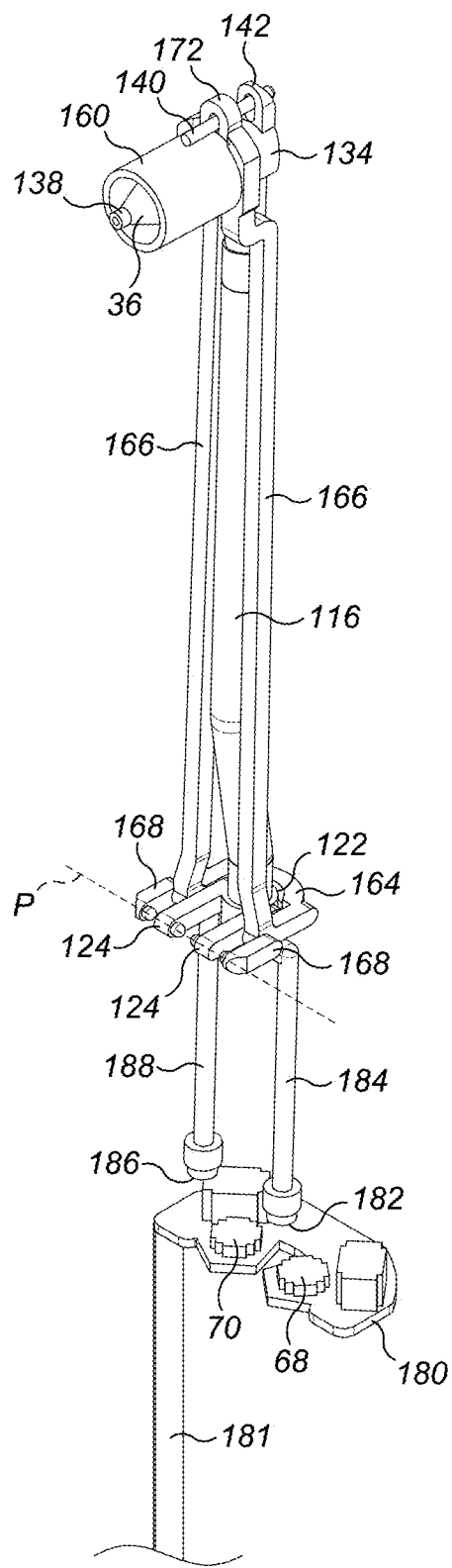
FIG. 5(c) is a perspective view of internal components of both the handle and the tool when in the second configuration.

The nozzle support 120 thus supports the nozzle 36 and the outlet section 116 of the tool conduit section 84 for movement relative to the handle 12 about the pivot axis P. The nozzle 36 is moveable relative to the handle 12 between a first, or distal, position as shown in FIG. 4(a), and a second, or proximal, position as shown in FIG. 5(a). In this embodiment, the nozzle 36 is biased for movement towards the distal position by the resilient section 118 of the tool conduit section 84, which is connected to the outlet section 116 of the tool conduit section 84 and the nozzle support 120 so as to be in an elastically deformed configuration. The internal force created within the resilient section 118 of the tool conduit section 84 acts in such a direction to urge the nozzle 36 towards the distal position.

The outlet section 116 of the tool conduit section 84 is connected to a fluid inlet 130 of the nozzle 36. The fluid inlet 130 is preferably a tangential inlet which conveys fluid tangentially into a fluid chamber 132 defined by a relatively rigid inlet section 134 of the nozzle 36. The inlet section 134 of the nozzle 36 is connected to a relatively flexible, elongate outlet section 136. The fluid outlet 42 of the nozzle 36 is located at the tip 138 of the outlet section 136. The outlet section 136 of the nozzle 36 is shaped such that at least the tip 138 of the nozzle 36 can move into, and out from, a typical interproximal gap as the appliance 10 is moved along the teeth of the user. The tip 138 of the nozzle preferably has a diameter in the range from 0.5 to 1.5 mm, and in this embodiment is around 1 mm. The movement of the nozzle 36 relative to the handle 12 is guided by a pin 140 connected to the stem 26, and which passes through an aperture defined by a hooked or looped section 142 of the inlet section 134 of the nozzle 36.

The head 28 of the tool 14 also comprises a datum component 150. As described in more detail below, the datum component 150 is also moveable relative to the handle 12, preferably in the same direction in which the nozzle 36 is moveable relative to the handle 12. The datum component 150 is moveable relative to the handle 12 separately from the nozzle 36, and thus during use of the appliance 10 there is relative movement between the nozzle 36 and the datum component 150.

The datum component 150 is preferably located adjacent to the nozzle 36, preferably between the nozzle 36 and the bristles 32 of the brush unit. In this embodiment, the datum component 150 surrounds the nozzle 36, and is tubular in shape, having a central bore 152 within which the nozzle 36 is disposed. The datum component 150 comprises a datum surface 154 for engaging the user's teeth during use of the appliance 10. In this embodiment, the datum surface 154 is annular in shape. The datum surface 154 is defined by the external surface of one end of an annular body 156 of the datum component 150. The other end of the body 156 engages the pin 140. The body 156 also comprises a resilient bellows portion 158 located between the ends of the body 156. The bellows portion 158 is annular in shape, and extends around a relatively rigid internal sleeve 160 of the datum component 150. The nozzle 36 comprises a circumferential flange 162 for engaging the inner wall of the sleeve 160 to inhibit the ingress of fluid or other matter into the stem 26 via the sleeve 160.

The datum component 150 is supported for movement relative to the handle 12 by a datum component support 164. The datum component 150 is connected to the datum component support 164 by a pair of arms 166 which extend between the datum component support 164 and the sleeve 160 of the datum component 150. The datum component support 164 is generally U-shaped, and extends partially about the nozzle support 120. Similar to the nozzle support 120, the datum component support 164 comprises a pair of fingers 168, each of which is pivotably connected to a respective bracket 170 mounted on, and preferably integral with, the platform 128 to allow the datum component support 164 to pivot about the pivot axis P.

The datum component support 164 thus supports the datum component 150 for movement relative to the handle 12 about the pivot axis P. The datum component 150 is moveable relative to the handle 12 between a first, or distal, position as shown in FIG. 4(a), and a second, or proximal, position as shown in FIG. 5(a). In this embodiment, the datum component 150 is biased for movement towards the distal position by the bellows portion 158 of the body 156, which becomes compressed as the datum component 150 moves from its distal position to its proximal position. The internal force created within the compressed bellows portion 158 of the body 156 acts in such a direction to urge the datum component 150 towards the distal position. The movement of the datum component 150 relative to the handle 12 is also guided by the pin 140, which passes through an aperture defined by a hooked or looped member 172 located at the ends of the arms 166 proximate to the sleeve 160 of the datum component 150.

The datum component 150 is preferably shaped such that the datum component 150 does not move into a typical interproximal gap as the appliance 10 is moved along the teeth of the user, but instead provides a bridge between the teeth on either side of the gap. The width of datum surface 154 of the datum component 150 is preferably in the range from 5 to 10 mm, and in a preferred embodiment is around 7 mm.

Figure 6A:
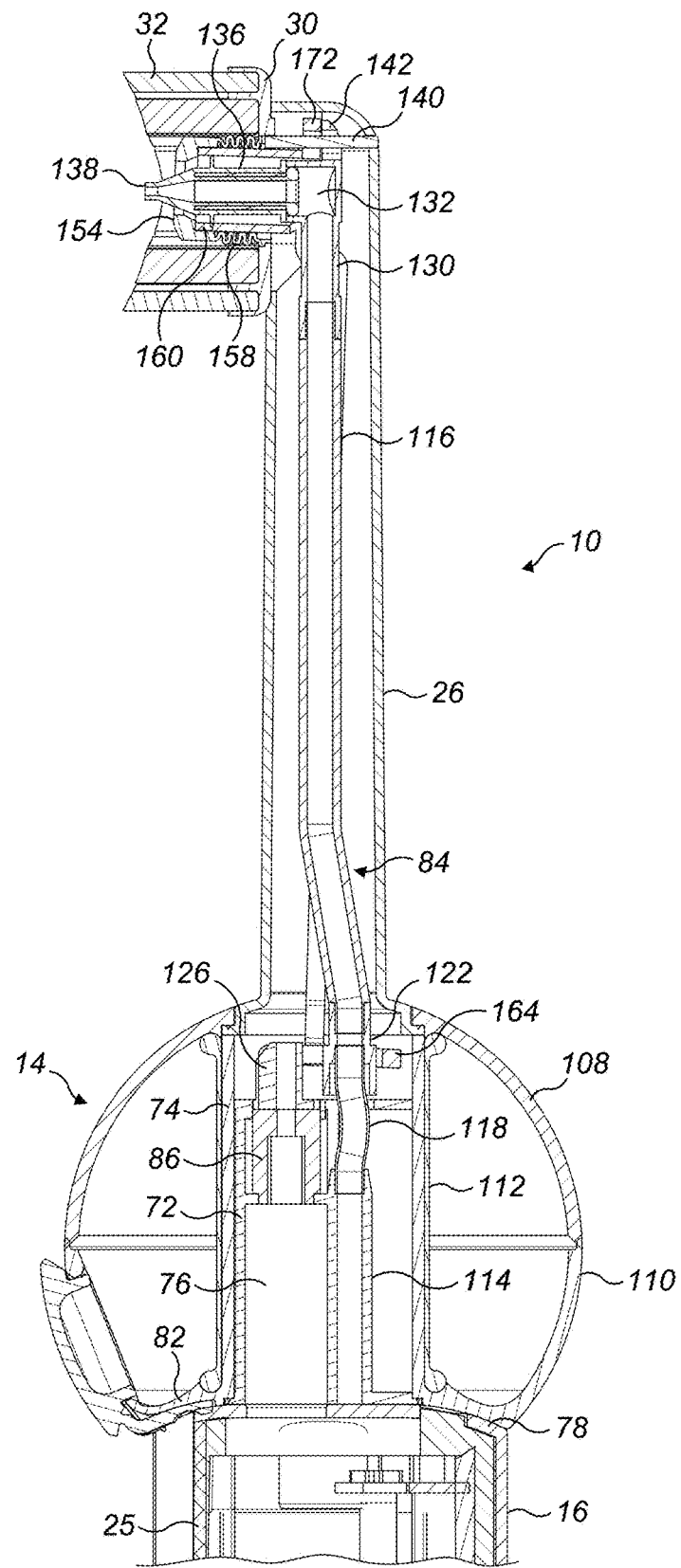
FIG. 6(a) is a side sectional view of the tool, in a third configuration in which the nozzle is in the distal position and the datum component is in the proximal position.
Figure 6B:
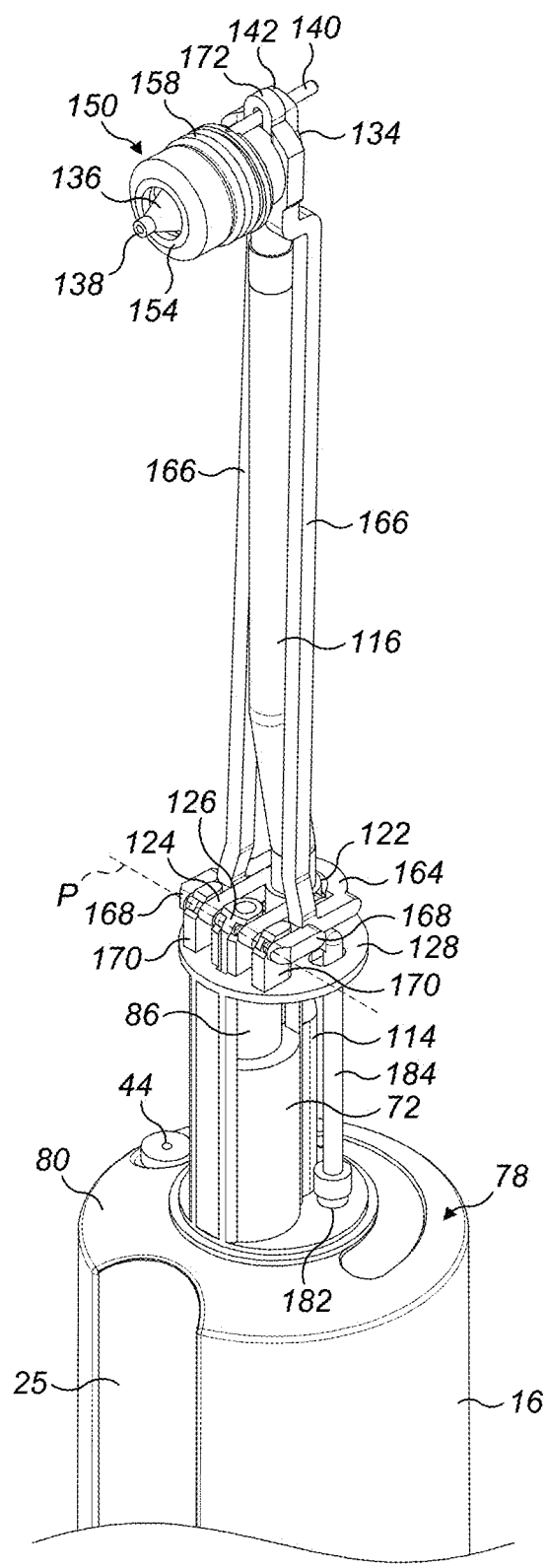
FIG. 6(b) is a perspective view of internal components of the tool when in the second configuration.
Figure 6C:
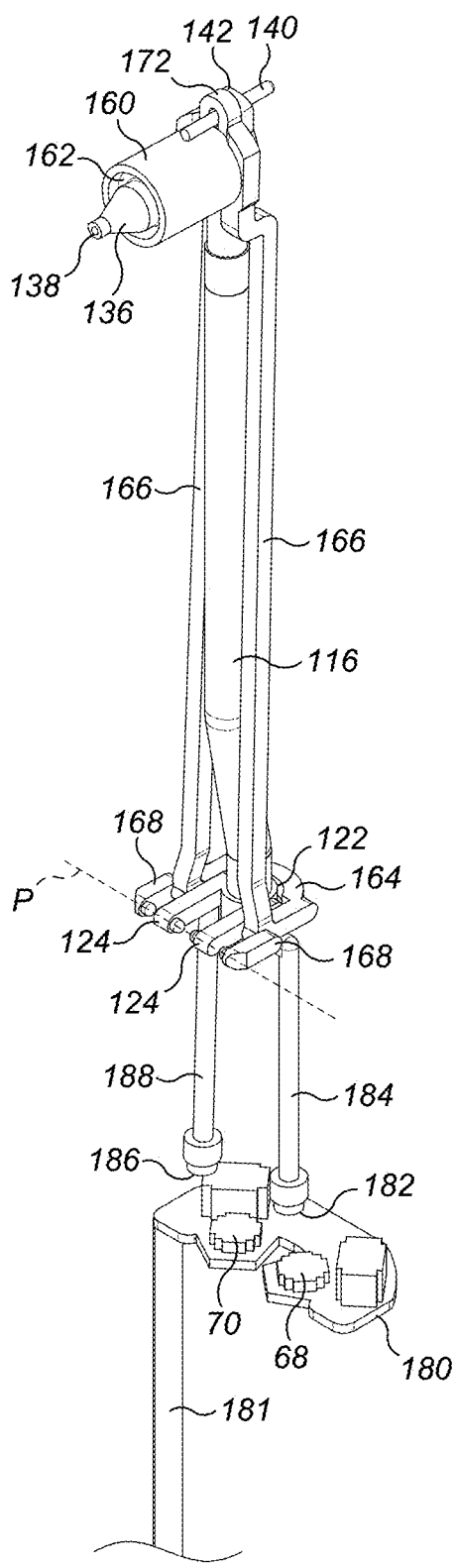
FIG. 6(c) is a perspective view of internal components of both the handle and the tool when in the second configuration.

The nozzle 36 and the datum component 150 are also moveable independently relative to each other. For example, FIGS. 6(a) to 6(c) illustrate the tool 14 in a configuration in which the nozzle 36 is in its proximal position and the datum component 150 is in its distal position. In a configuration of the tool 14 in which both the nozzle 36 and the datum component 150 are in their distal positions, as shown in FIG. 4(a), the tip 138 of the nozzle 36 is substantially coplanar with the datum surface 154 of the datum component 150. In a configuration of the tool 14 in which both the nozzle 36 and the datum component 150 are in their proximal positions, as shown in FIG. 5(a), there is only a relatively small distance between the tip 138 of the nozzle 36 and the datum surface 154 of the datum component 150, whereas in the configuration of the tool 14 in which the nozzle 36 is in its proximal position, and the datum component 150 is in its distal position, there is a relatively large distance between the tip 138 of the nozzle 36 and the datum surface 154 of the datum component 150.

The movements of the nozzle 36 and the datum component 150 relative to the handle 12 are detected by sensors 68, 70 of the control circuit. A first sensor 68 is provided for detecting movement of the nozzle support 120, and thus the nozzle 36, relative to the handle 12. The first sensor 68 is mounted on a circuit board 180 which is located within the handle 12 adjacent the end surface 78 of the body 16 of the handle 12, and connected to the controller 66 by connector 181. In this embodiment, the first sensor 68 is in the form of a Hall effect sensor which detects the movement of a first magnet 182 connected to the end of a first arm 184 depending from the nozzle support 120, and which generates an output having a voltage which is dependent on the relative positions of the first sensor 68 and the first magnet 182.

A second sensor 70 is provided for detecting movement of the datum component support 164, and thus the datum component 150, relative to the handle 12. The second sensor 70 is also mounted on the circuit board 180, and is in the form of a Hall effect sensor which detects the movement of a second magnet 186 connected to the end of a second arm 188 depending from the datum component support 164, and which is moveable relative to the first magnet 182. The second sensor 70 generates an output having a voltage which is dependent on the relative positions of the second sensor 70 and the second magnet 186.

The controller 66 is configured to receive outputs from the sensors 68, 70, and to sample those outputs every 10 ms, or at a frequency of 100 Hz, to generate sampled outputs, or sampled voltages, S, every 10 ms. The controller 66 is configured to process the sampled outputs to detect relative movement between the nozzle 36 and the datum component 150. For example, from the sampled outputs the controller 66 may calculate a modified sample output, or voltage, Sm, which varies depending on relative movement between the nozzle 36 and the datum component 150, for example by subtracting the sampled output from one of the sensors 68, 70 from the sampled output from the other one of the sensors 68, 70.

From the modified sampled outputs, the controller 66 is configured to generate a rate of change, Sr, of the modified sampled outputs from the difference between consecutive modified sampled outputs. Thus, the control circuit is configured to calculate a value for Sr every 10 ms. The controller 66 is further configured to determine an average rate of change of the modified sampled outputs, Sa, by calculating the average value of the 10 most recent values of Sr. A value for Sa is thus also calculated every 10 ms from the values of Sr calculated during the preceding 100 ms time period.

In use, the user first fills the fluid reservoir 34 with working fluid, which in this embodiment is water. With the closure member 102 in the open position, the user may place the appliance 10 beneath the spout of a tap and turn on the tap so that water from the spout enters the exposed fluid inlet port 100 of the fluid reservoir 34. As at least part of the external wall of the fluid reservoir 34 is transparent, the user can observe the filling of the fluid reservoir 34. When the fluid reservoir 34 is full, the user returns the closure member 102 to the closed position to seal the fluid inlet port 100.

The user switches on the appliance 10 by depressing button 18, the action of which is detected by the controller 66. The user can then select a mode of operation of the appliance 10 by depressing button 20. For example, the user may choose to activate the movement of the brush unit by depressing button 20. The currently selected mode of operation of the appliance 10 is displayed on the display 24, and the user can toggle between the various selectable modes of operation by depressing button 20 until the desired operational mode is displayed on the display 24. In this embodiment, there are six different user selectable operational modes:

| MODE | BRUSHING | MANUAL JET | AUTO JET |
| --- | --- | --- | --- |
| 1 | ON | OFF | OFF |
| 2 | ON | ON | OFF |
| 3 | ON | OFF | ON |
| 4 | OFF | ON | OFF |
| 5 | OFF | OFF | ON |
| 6 | ON | ON | ON |

When any of modes 1 to 3 or 6 are selected, the controller 66 activates the motor to move the brush unit relative to the handle 12 to brush teeth.

When any of modes 2 to 6 are selected, initially the controller 66 operates the motor 50 to activate the pump 48 to draw a volume of water, in this example around 0.25 ml, from the fluid reservoir 34 into a fluid chamber of the pump 48. The pump 48, which is preferably a positive displacement pump, is preferably held in a primed configuration, in which the volume of water is held under pressure within the pump 48, preferably at a static pressure in the range from 3 to 10 bar.

When mode 2, mode 4 or mode 6 is selected by the user, a burst of water is emitted from the nozzle 36 in response to user depression of the button 22. The depression of the button 22 is detected by the controller 66, which may operate the motor 50 to activate the pump 48 to eject the stored volume of water from the fluid outlet 62 of the pump 48 in the form of a burst of water. The burst of water passes through the second conduit 60 to be ejected from the fluid outlet 42 of the nozzle 36. When the nozzle 36 is positioned within, or aligned with, an interproximal gap, the burst of water ejected from the nozzle 36 can dislodge matter located within the interproximal gap. The controller 66 is arranged to replenish the fluid chamber of the pump 48 following the delivery of the burst of water to the nozzle 36 to return the pump 48 to its primed configuration.

When mode 3, mode 5 or mode 6 is selected by the user, a burst of water is emitted from the nozzle 36 depending on the outputs from the sensors 68, 70. Thus, when mode 6 is selected, a burst of water is emitted from the nozzle 36 depending on the outputs from the sensors 68, 70 or in response to user depression of the button 22.

The controller 66 is initially in a first, or "unprimed", condition. As the head 28 of the appliance 10 is pushed against a user's tooth, the bristles 36, the tip 138 of the nozzle 36 and the datum surface 154 of the datum component 150 engage the user's tooth. The nozzle 36 thus provides a contact member of the dental treatment system, which in this embodiment comprises a fluid delivery system 40, of the appliance 10. Depending on the force that the user applies to the head 28 of the appliance 10 as it is pushed against the user's teeth, the bristles 32 of the brush unit will flex, and both the nozzle 36 and the datum component 150 will move from their distal positions towards their proximal positions. As the tip 138 of the nozzle 36 and the datum surface 154 of the datum component 150 are substantially coplanar when the nozzle 36 and the datum component 150 are in their distal positions, the nozzle 36 and the datum component 150 will move in unison away from their distal positions, and so there is little, if any, relative movement between the nozzle 36 and the datum component 150, and so the controller remains in the unprimed condition.

As the head 28 of the appliance 10 is moved across the user's tooth, the positions of the nozzle 36 and the datum component 150 relative to the handle 12 will vary depending on the shape and contours of the tooth and the force with which the head 28 is pressed against the tooth. However, with both the tip 138 of the nozzle 36 and the datum surface 154 of the datum component 150 both engaging the user's tooth, the nozzle 36 and the datum component 150 will move in unison relative to the handle, and so again there is little, if any, relative movement between the nozzle 36 and the datum component 150.

As the head 28 of the appliance 10 moves from the user's tooth to the adjacent tooth, the datum component 150 will bridge the interproximal gap between those teeth, and so there will be relatively little movement of the datum component 150 relative to the handle 12. However, as the appliance 10 moves across the user's teeth, the nozzle 36 becomes positioned over the interproximal gap between those teeth. In that position, the force acting on the nozzle 36, through its engagement with the teeth of the user, is removed. This allows the resilient section 118 of the tool conduit section 84 to urge the nozzle support 120 to pivot about the pivot axis P, which moves the nozzle 36 rapidly towards its distal position, as shown in FIG. 6(a). This causes the first magnet 182 to move rapidly relative to the first sensor 68, but with relatively little, or no, movement of the second magnet 186 relative to the second sensor 70.

This generates a rapid variation in the value of Sa calculated by the controller 66. In this embodiment, Sa has a relatively large negative value when the nozzle 36 moves rapidly towards its distal position. When the value of Sa falls below a first threshold value, which occurs when the tip of the nozzle 36 enters an interproximal gap, the controller 66 enters a second, or "primed", condition. With the tip of the nozzle 36 now located within the interproximal gap, the value of Sa increases rapidly. This can be to a value of approximately zero, or to a value greater than zero as the nozzle 36 moves away its distal position as the tip of the nozzle 36 begins to move over the adjacent tooth.

When the value of Sa subsequently rises above a second threshold value, which is greater than the first threshold value, the controller 66 enters a third, or "ejection", condition in which the controller 66 operates the motor 50 to activate the pump 48 to eject the stored volume of water from the fluid outlet 62 of the pump 48 in the form of a burst of water. The burst of water passes through the second conduit 60 to be ejected from the fluid outlet 42 of the nozzle 36.

Following the delivery of the burst of water to the nozzle 36, the controller 66 is arranged to replenish the fluid chamber of the pump 48 to return the pump 48 to its primed configuration. Once the fluid chamber of the pump 48 has been replenished, the controller 66 returns to its unprimed condition.

Figure 7A:
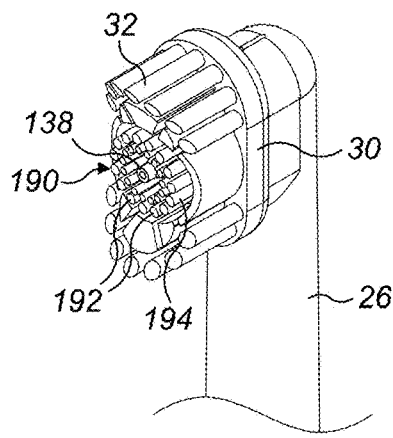
FIGS. 7(a) and 7(b) are a perspective view and a front view respectively of a head of the appliance with a first alternative datum component.
Figure 7B:
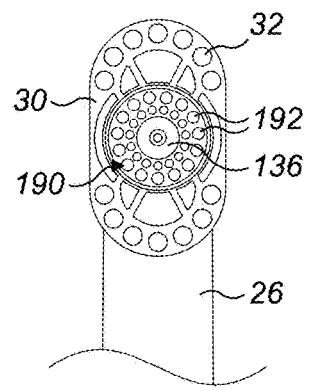
Figure 8A:
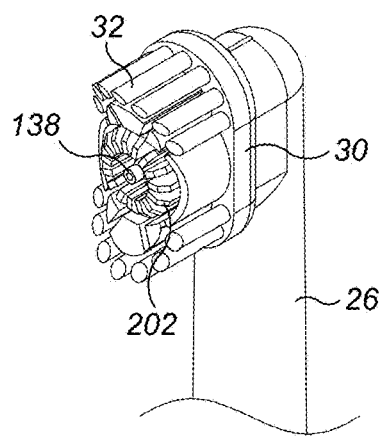
FIGS. 8(a) and 8(b) are a perspective view and a front view respectively of a head of the appliance with a second alternative datum component.
Figure 8B:
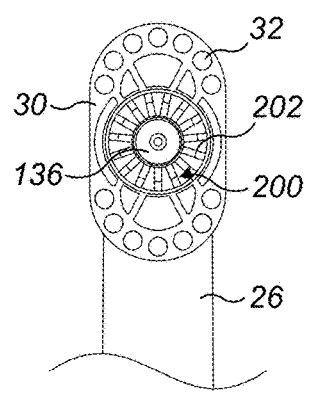
Figure 9A:
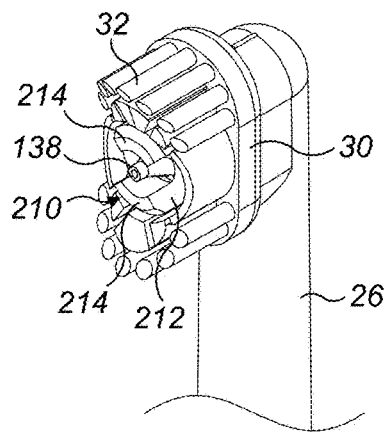
FIGS. 9(a) and 9(b) are a perspective view and a front view respectively of a head of the appliance with a third alternative datum component.
Figure 9B:
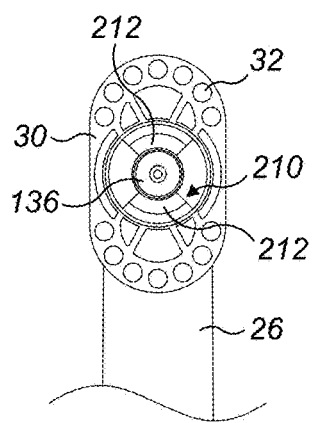

In the above embodiment, the datum component 150 comprises a single annular datum surface 154. Alternatively, the datum component 150 may comprise a plurality of datum surfaces. FIGS. 7(a) and 7(b) illustrate a head of the appliance with a first alternative datum component 190, in which the datum component 190 comprises a plurality of datum surfaces 192 each provided by a respective finger 194 of the datum component 190. The fingers 194 may be relatively rigid members connected to a common bellows portion of the datum component 190. Alternatively, the fingers 194 may be relatively flexible, formed, for example, from elastomeric material. In this datum component 190, the fingers 194 are generally cylindrical in shape, and have one of a plurality of different sizes. FIGS. 8(a) and 8(b) illustrate a head of the appliance with a second alternative datum component 200, in which the fingers 202 of the datum component 200 are in the form of radially arranged fins, which also may be connected to a common bellows portion of the datum component 200. FIGS. 9(a) and 9(b) illustrate a head of the appliance with a third alternative datum component 210, and which a single contact member 212 comprises a plurality of angularly spaced datum surfaces 214.

Figure 10:
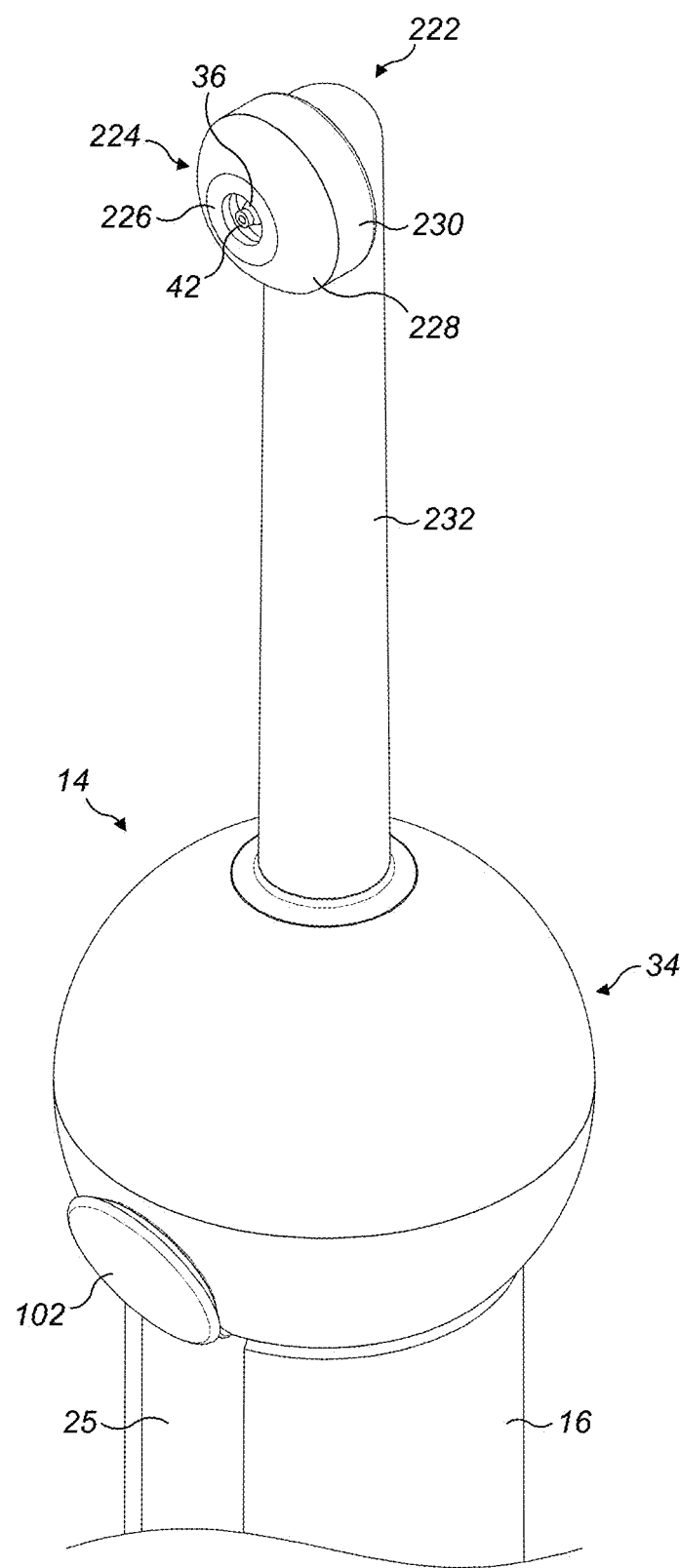
FIG. 10 is a perspective view of the tool of a second embodiment of a dental treatment appliance.
Figure 11A:
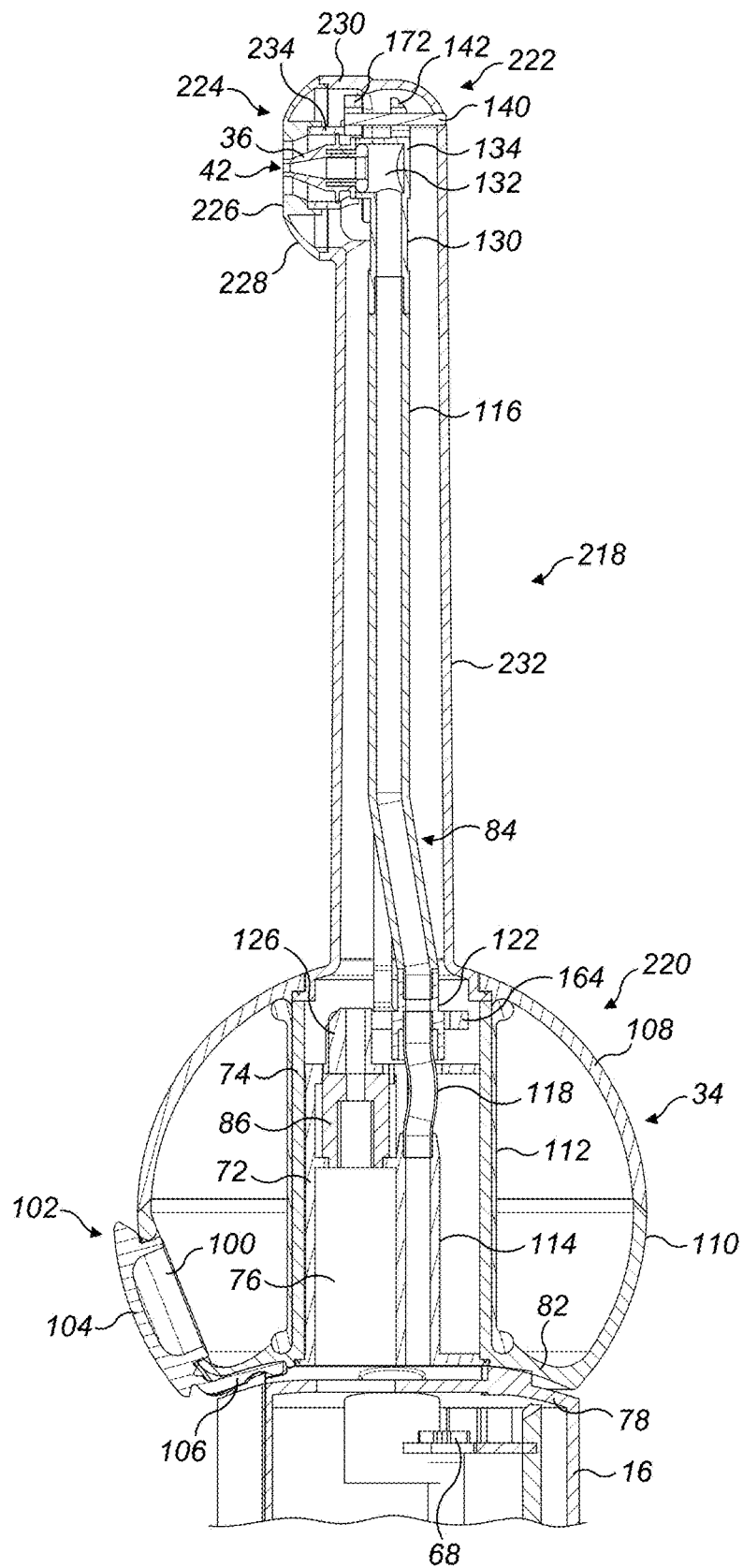
FIG. 11(a) is a side sectional view of the tool of FIG. 10, in a first configuration in which both a nozzle and a datum component of the appliance are in a distal position.
Figure 11B:
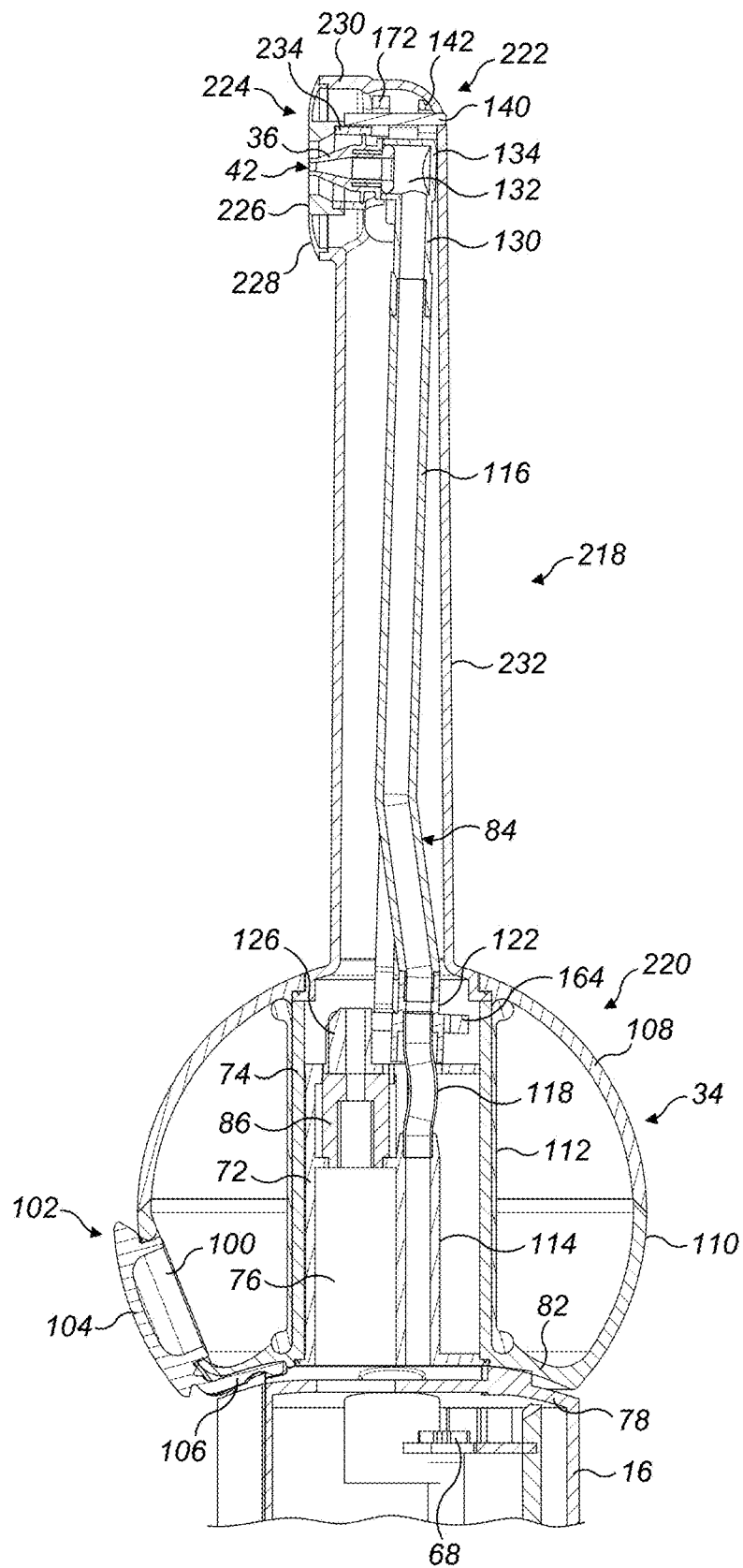
FIG. 11(b) is a side sectional view of the tool of FIG. 10, in a second configuration in which both the nozzle and the datum component are in a proximal position.
Figure 11C:
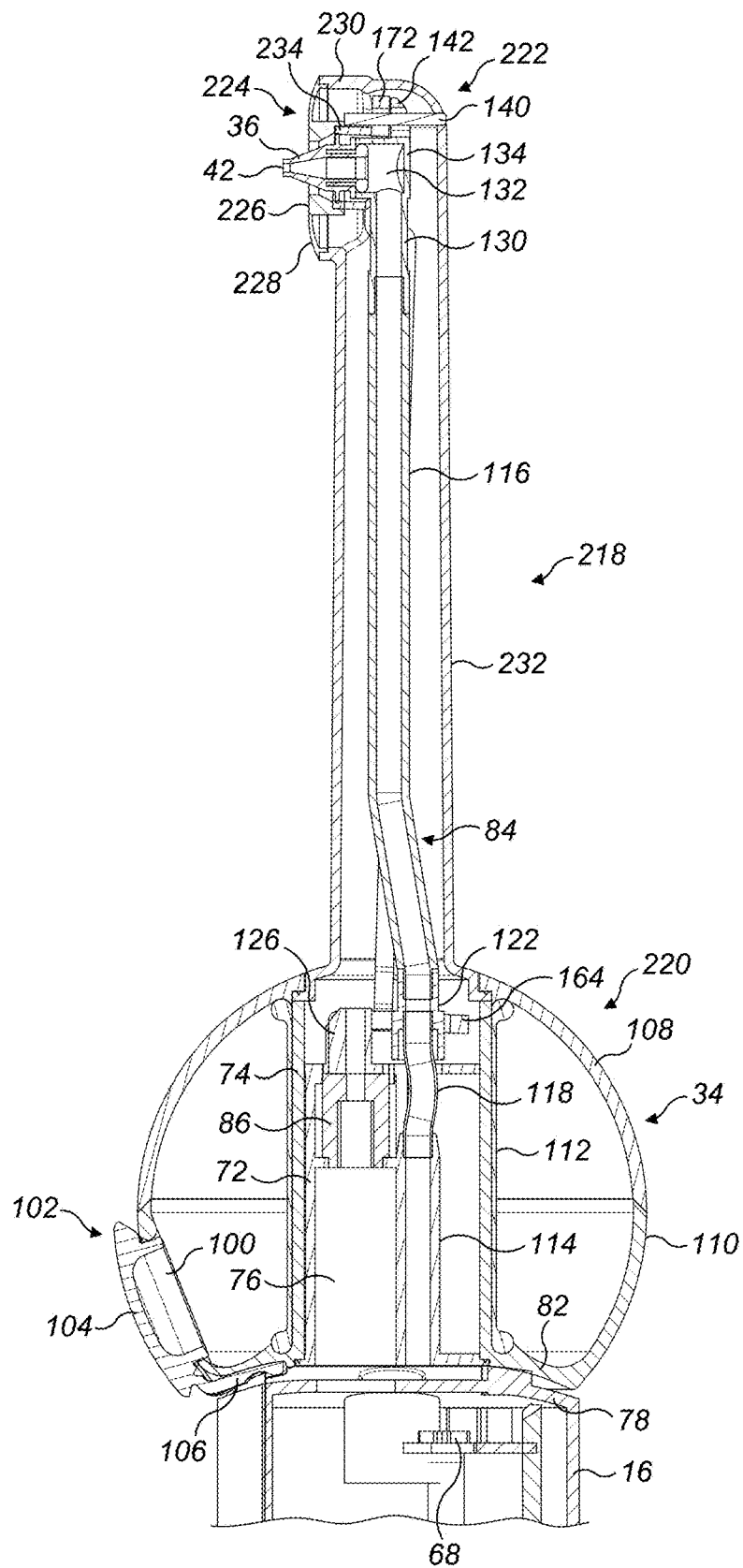
FIG. 11(c) is a side sectional view of the tool of FIG. 10, in a third configuration in which the nozzle is in the distal position and the datum component is in the proximal position.

As mentioned above, in other embodiments the tool may be provided without a brush unit so that the appliance is in the form of a dedicated interproximal treatment appliance for cleaning between the gaps in the user's teeth. Such an embodiment of a dental treatment appliance 218 is illustrated in FIGS. 10 to 11(c). In this embodiment, the tool 220 differs from the tool 14 insofar as a brush unit is not connected to the head 222 of the tool, and the datum component 150 is replaced by a relatively larger datum component 224. Similar to the datum component 150, the datum component 224 surrounds the nozzle 36 and has a central bore within which the nozzle 36 is disposed. The datum component 224 comprises a datum surface 226 for engaging the user's teeth during use of the appliance 10. In this embodiment, the datum surface 226 is also annular in shape. The datum surface 226 is defined by the external surface of one end of an annular body 228 of the datum component 224. The other end of the body 228 is connected to an annular end portion 230 of the head 222 of the tool 220. The end portion 230 of the head 222 is connected to, and preferably integral with, the stem 232 of the tool 220. The contact member 228 is connected to, and extends around, a relatively rigid internal sleeve 234 of the datum component 224, which is engaged by the circumferential flange 162 of the nozzle 36.

The sleeve 234 of the datum component 224 is connected to the same datum component support as the sleeve 160 of the datum component 150 to allow the datum component 224 to move relative to the handle 12 about the pivot axis P. Similar to the datum component 150, the datum component 224 is moveable relative to the handle 12 between a first, or distal, position as shown in FIG. 11(*a*), and a second, or proximal, position as shown in FIGS. 11(*b*) and 11(*c*). The nozzle 36 and the datum component 224 are also moveable independently relative to each other. When both the nozzle 36 and the datum component 224 are in their distal positions, the tip 42 of the nozzle 36 and the datum surface 226 are substantially coplanar.

The movements of the nozzle 36 and the datum component 224 relative to the handle 12 are detected using the same arrangements of sensors 68, 70 and magnets 182, 186 as in the first embodiment. In this embodiment though, the datum component 224 is biased for movement towards the distal position by the body 228, which is formed from resilient material. As illustrated in FIGS. 11(*b*) and 11(*c*), the body 228 becomes compressed as the datum component 224 moves from its distal position to its proximal position. The internal force created within the compressed body 228 acts in such a direction to urge the datum component 224 towards the distal position. In this embodiment, engagement between the body 228 and the end of the pin 140 inhibits movement of the datum component 224 beyond its proximal position; whilst the body 228 may become further compressed, the sleeve 234 does not move beyond the position illustrated in FIGS. 11(*b*) and 11(*c*).

In each of the above embodiments, the movements of the nozzle 36 and the datum component 150, 224 are detected separately, and from the signals output from the sensors 68, 70, relative movement between the nozzle 36 and the datum component 150, 224 is detected. In the embodiment of a dental treatment appliance 240 illustrated in FIGS. 12(*a*) to 14, a single sensor is used to detect relative movement between the nozzle and the datum component. Similar to the appliance 10, the appliance 240 comprises a handle 242 and a tool 244 detachably connected to the handle 242. The tool 244 varies from the tool 14 of the appliance 10 insofar as the magnets 182, 186 and the arms 184, 188 to which the magnets 182, 186 are connected are replaced by a single magnet 246 connected to one of the nozzle 36 and the datum component 150, in this embodiment to the datum component 150. The magnet 246 may be mounted on the datum component 150, or to any part of the tool 244 to which the datum component 150 is connected and moves with the datum component 150. In this embodiment, the pin 140 is removed, and the magnet 246 is connected to a modified end section 172' of the arms 166 connected to the datum component support 164. A sensor 248 for outputting a signal which depends on the position of the magnet 246 relative to the sensor 248 is connected to the nozzle 36. Again, the sensor 248 may be mounted on the nozzle 36, or to any part of the tool 244 to which the nozzle 36 is connected to and moves with the nozzle 36. The sensor 248 is preferably located proximate to the magnet 246, and so in this embodiment the sensor 248 is mounted on the inlet section 134 of the nozzle 36. The sensor 248 is preferably a Hall effect sensor.

The sensor 248 is connected by a flexible cable 250 to a connector 252, which connects physically to a complimentary connector (not shown) located on the handle 242 when the tool 244 is mounted on the handle 242. Alternatively, the connector 252 may be replaced by a transmitter for transmitting signals output from the sensor 248 to the controller 66. The complimentary connector is preferably provided on the circuit board 180, from which the sensors 68, 70 have been removed; otherwise the handle 242 is the same as the handle 12 of the appliance 10.

The sensor 248 generates an output having a voltage which is dependent on the relative positions of the magnet 246 and the sensor 248. The controller 66 is configured to receive outputs from the sensor 248, and to sample those outputs every 10 ms, or at a frequency of 100 Hz, to generate a sampled output, or sampled voltage, S, every 10 ms.

From the sampled outputs, the controller 66 is configured to generate a rate of change, Sr, of the sampled outputs from the difference between consecutive sampled outputs. Thus, the control circuit is configured to calculate a value for Sr every 10 ms. The controller 66 is further configured to determine an average rate of change of the sampled outputs, Sa, by calculating the average value of the 10 most recent values of Sr. A value for Sa is thus also calculated every 10 ms from the values of Sr calculated during the preceding 100 ms time period.

Figure 12A:
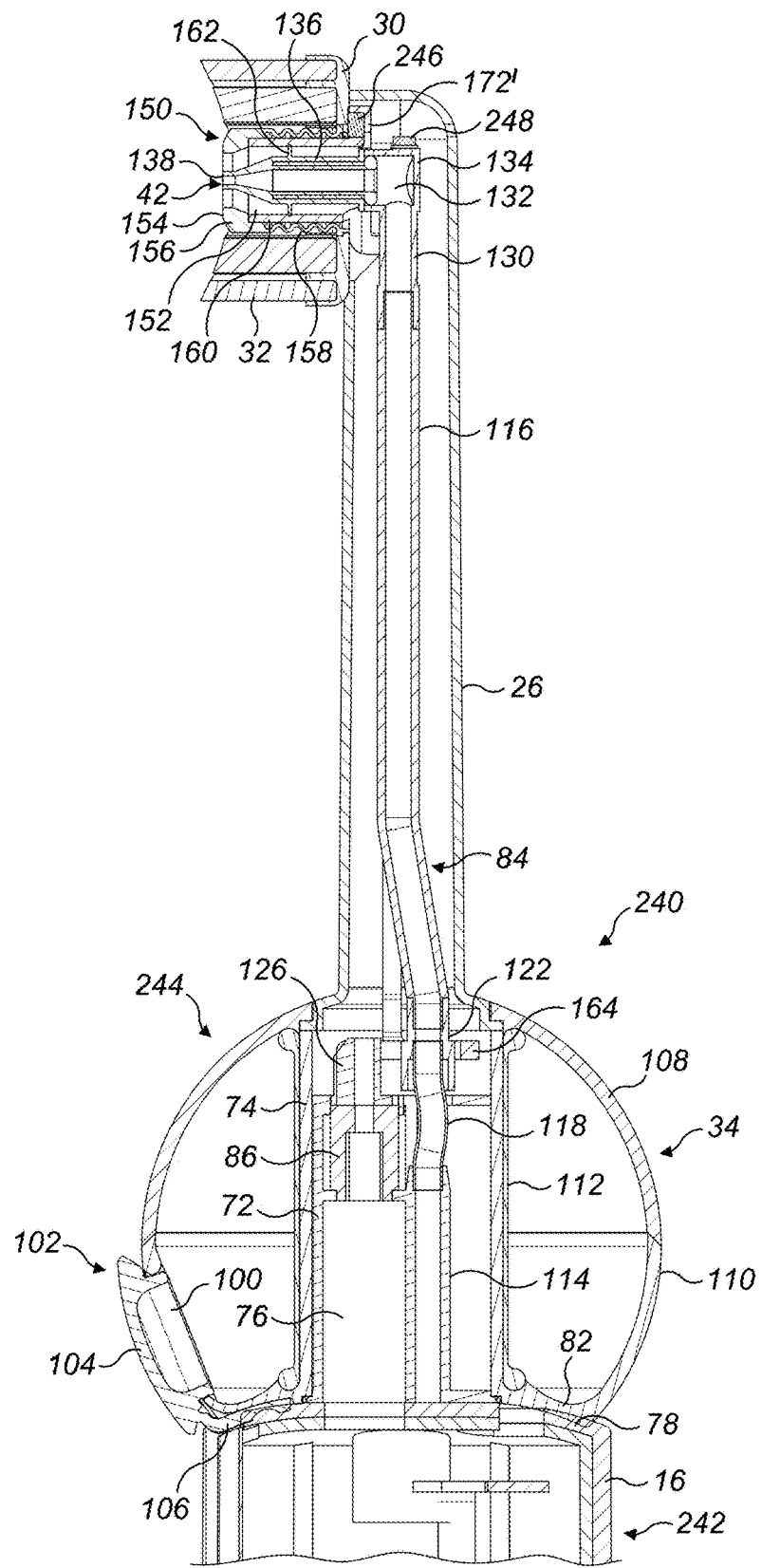
FIG. 12(a) is a side sectional view of a tool of a third embodiment of a dental treatment appliance, in a first configuration in which both a nozzle and a datum component of the appliance are in a distal position.
Figure 12B:
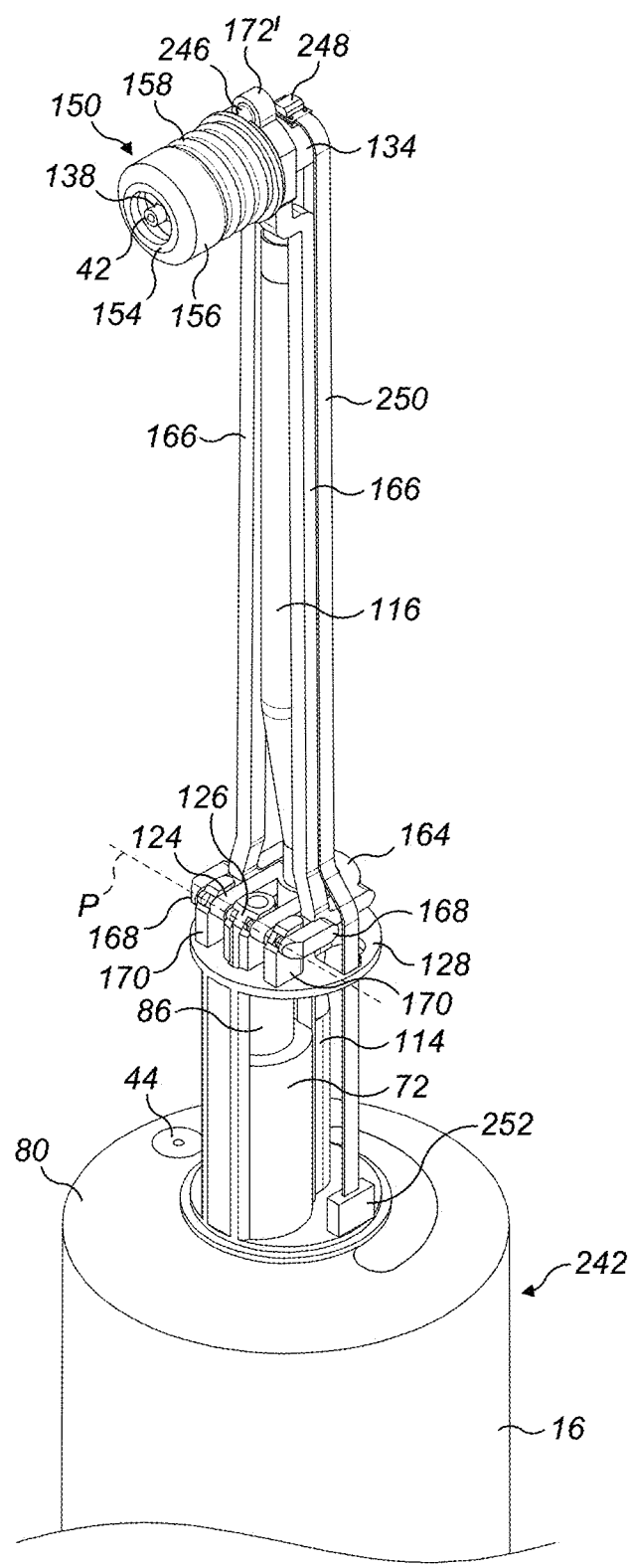
FIG. 12(b) is a perspective view of internal components of the tool of the appliance of FIG. 12(a) when in the first configuration.
Figure 12C:
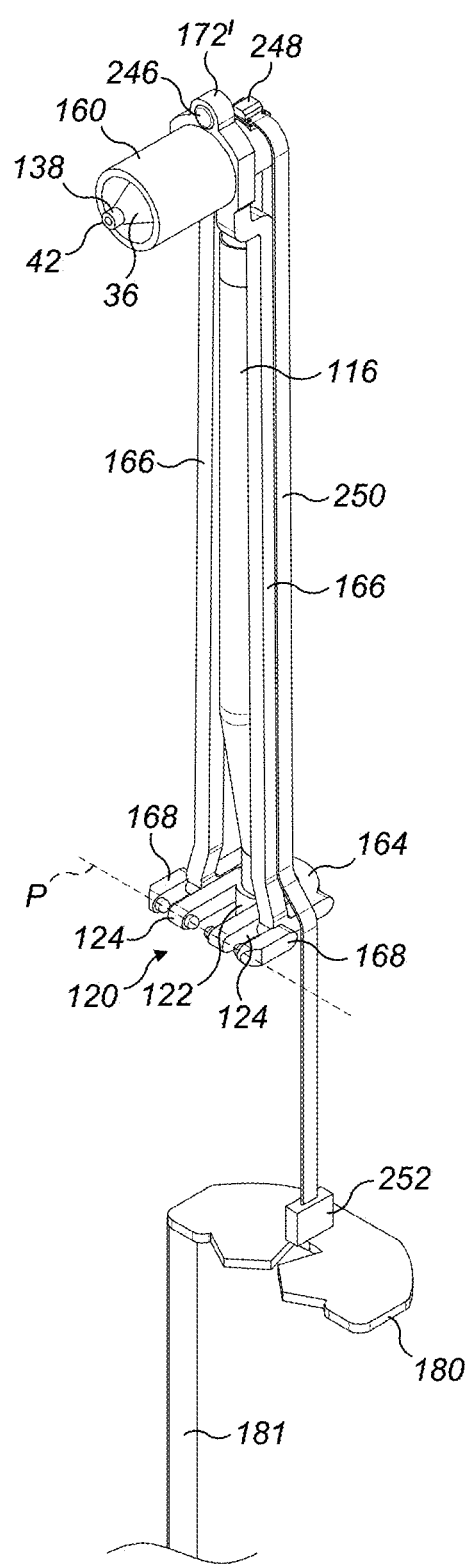
FIG. 12(c) is a perspective view of internal components of both the handle and the tool of the appliance of FIG. 12(a) when in the first configuration.
Figure 13:
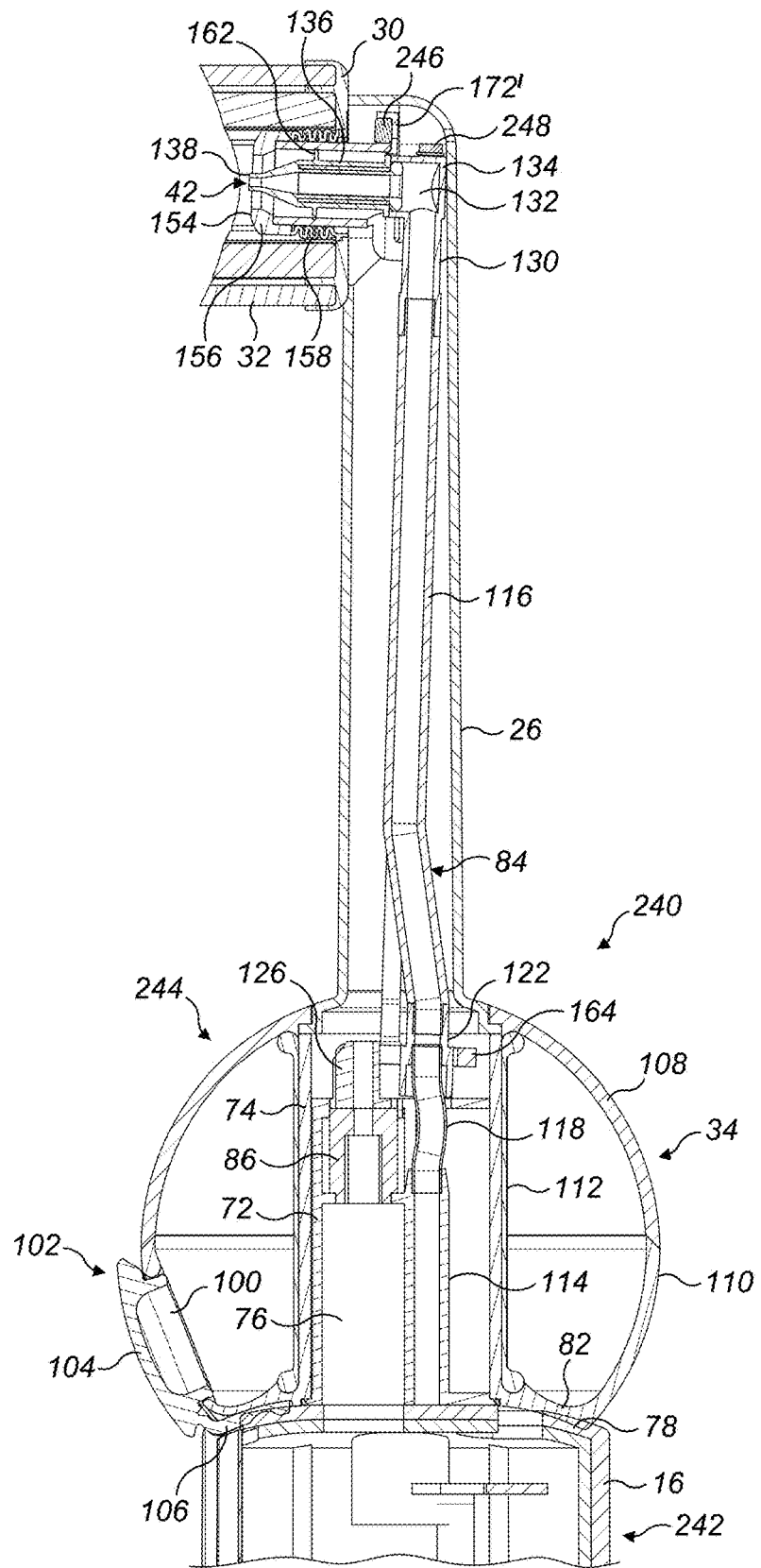
FIG. 13 is a side sectional view of the tool of the appliance of FIG. 12(a), in a second configuration in which both the nozzle and the datum component are in a proximal position.

The appliance 240 is usable in one of the six different modes discussed with reference to appliance 10. When mode 3, mode 5 or mode 6 is selected by the user, the controller 66 is initially in a first, or "unprimed", condition. As the head 28 of the appliance 240 is pushed against a user's tooth, the bristles 36, the tip 138 of the nozzle 36 and the datum surface 154 of the datum component 150 engage the user's tooth. Depending on the force that the user applies to the head 28 of the appliance 240 as it is pushed against the user's teeth, the bristles 32 of the brush unit will flex, and both the nozzle 36 and the datum component 150 will move from their distal positions, as shown in FIG. 12(*a*) towards their proximal positions, as shown in FIG. 13. As the tip 138 of the nozzle 36 and the datum surface 154 of the datum component 150 are substantially coplanar when the nozzle 36 and the datum component 150 are in their distal positions, the nozzle 36 and the datum component 150 will move in unison away from their distal positions, and so there is little, if any, relative movement between the nozzle 36 and the datum component 150. The output from the sensor 248 thus remains relatively uniform, and so the controller 66 remains in the unprimed condition.

Figure 15:
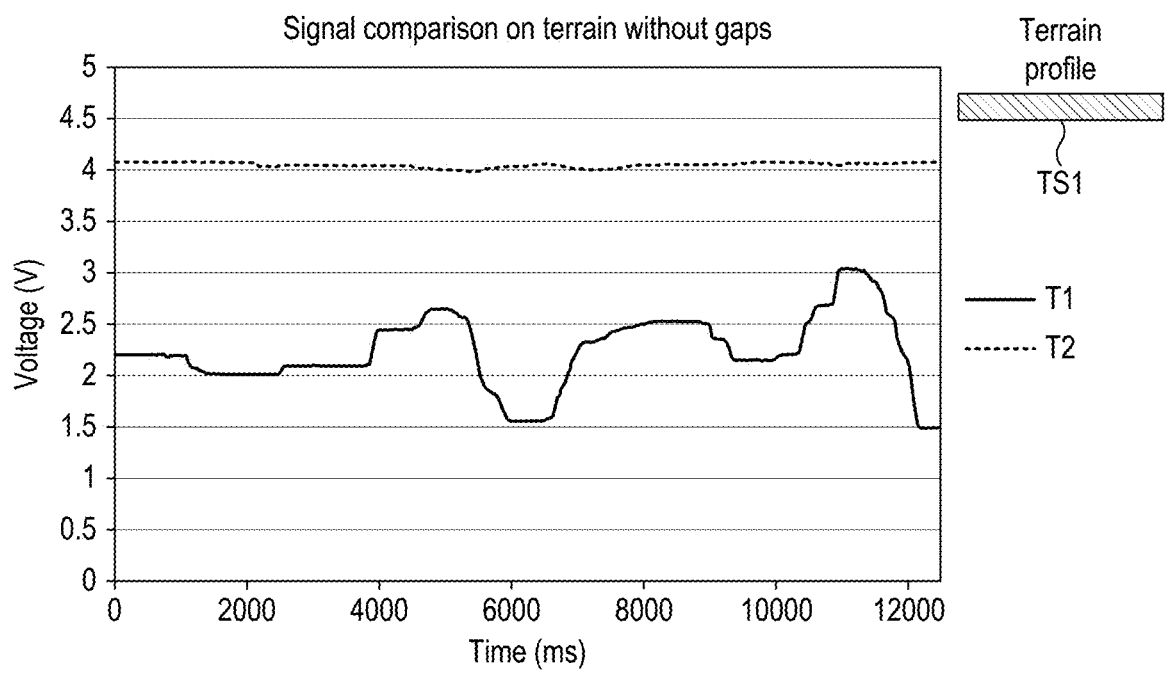
FIG. 15 is a graph illustrating the variation with time of a signal output from the sensor of the appliance of FIG. 12(a) when the head of the appliance is moved across a relatively flat surface.

As the head 28 of the appliance 240 is moved across the user's tooth, the positions of the nozzle 36 and the datum component 150 relative to the handle 242 will vary depending on the shape and contours of the tooth and the force with which the head 28 is pressed against the tooth. However, with both the tip 138 of the nozzle 36 and the datum surface 154 of the datum component 150 both engaging the user's tooth, the nozzle 36 and the datum component 150 will move in unison relative to the handle, and so again there is little, if any, relative movement between the nozzle 36 and the datum component 150. The output from the sensor 248 thus continues to remain relatively uniform, and so the controller 66 remains in the unprimed condition. To help illustrate this, trace T1 in FIG. 15 illustrates an example of a variation of the output from the sensor 248 as the head of the appliance 240 is moved across a relatively flat test surface TS1. In contrast, trace T2 illustrates the variation of the output received simultaneously from a reference sensor located on a stationary portion of the head of the appliance 240, for example adjacent the magnet 246 but on an internal surface of the stem 26 of the tool 244. While trace T1 remains relatively constant with time, trace T2 varies depending on the pressure which is applied to the tip of the nozzle 36 by the user as the head of the appliance 240 is moved across the relatively flat reference surface.

Figure 14:
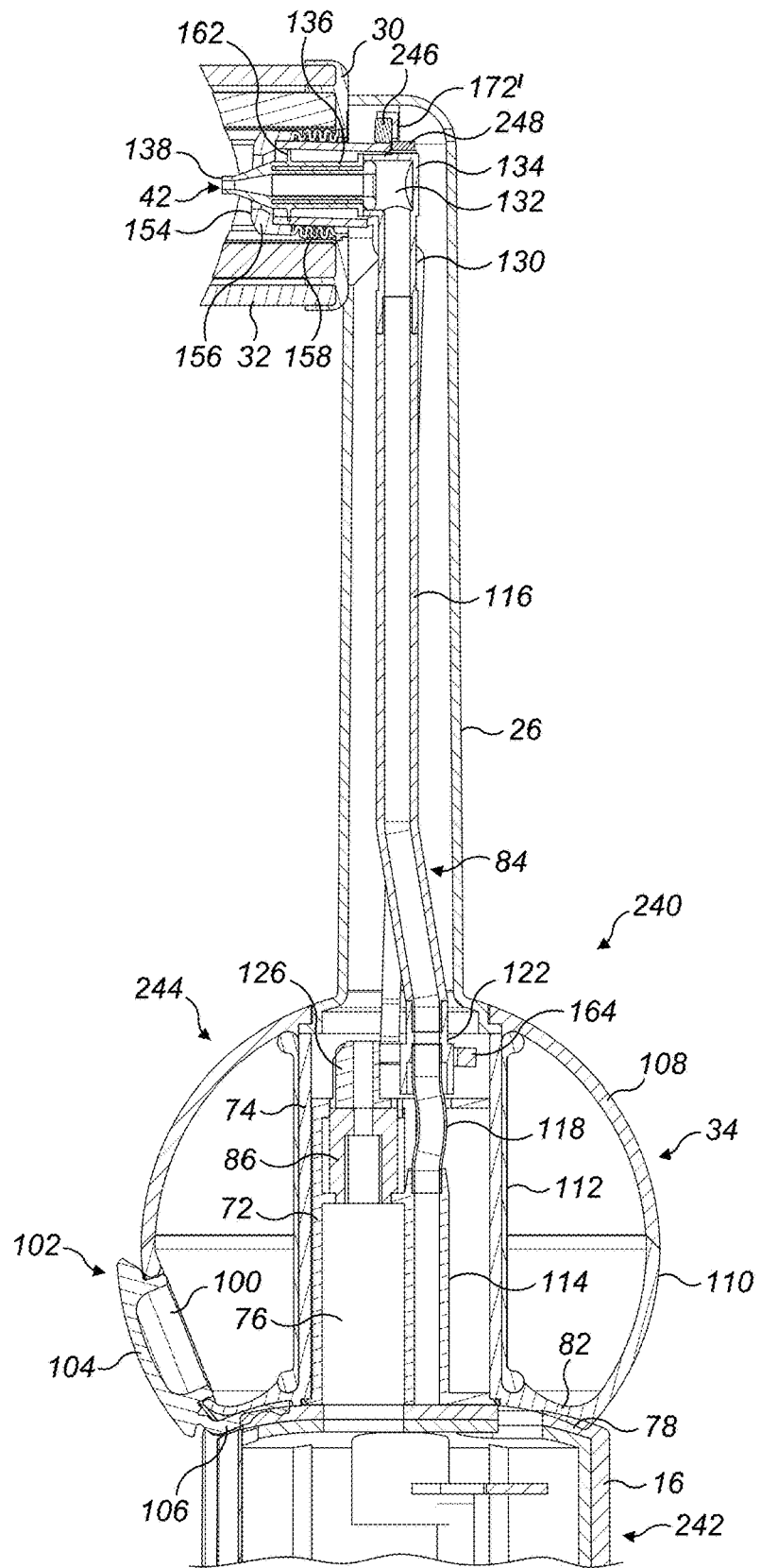
FIG. 14 is a side sectional view of the tool of the appliance of FIG. 12(a), in a third configuration in which the nozzle is in the distal position and the datum component is in the proximal position.
Figure 16:
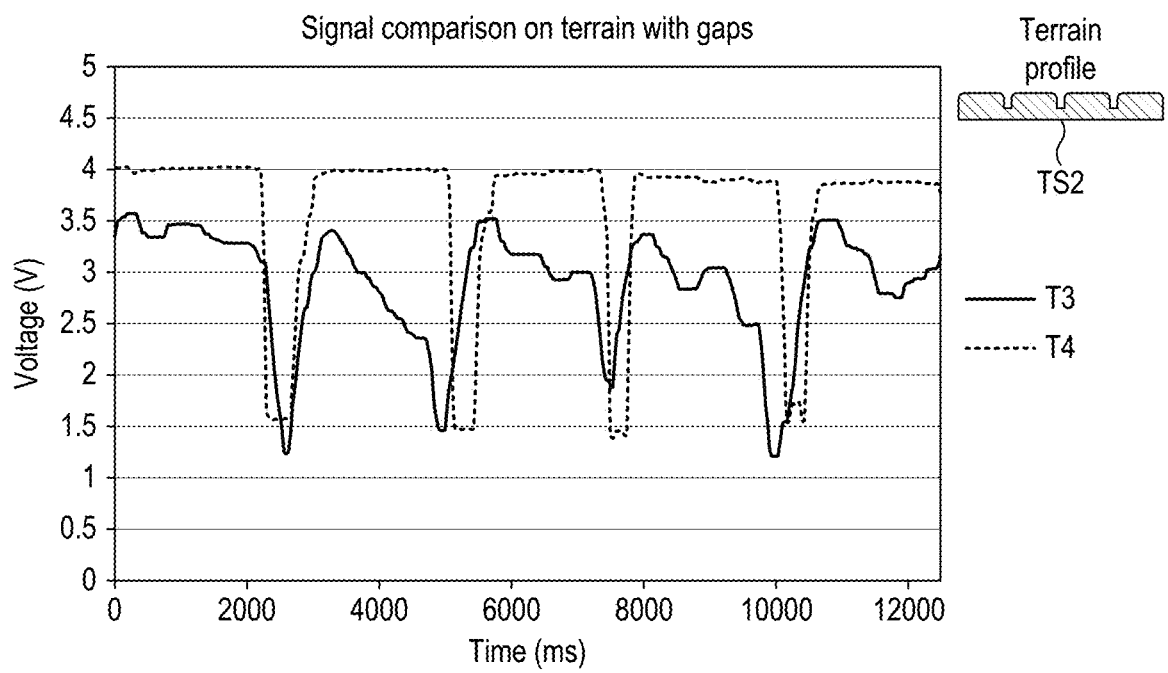
FIG. 16 is a graph illustrating the variation with time of a signal output from the sensor of the appliance of FIG. 12(a) when the head of the appliance is moved across a relatively uneven surface.

As the head 28 of the appliance 240 moves from the user's tooth to the adjacent tooth, the datum component 150 will bridge the interproximal gap between those teeth, and so there will be relatively little movement of the datum component 150 relative to the handle 242. However, as the appliance 240 moves across the user's teeth, the nozzle 36 becomes positioned over the interproximal gap between those teeth. In that position, the force acting on the nozzle 36, through its engagement with the teeth of the user, is removed. This allows the resilient section 118 of the tool conduit section 84 to urge the nozzle support 120 to pivot about the pivot axis P, which moves the nozzle 36 rapidly towards its distal position, as shown in FIG. 14. This causes the sensor 248 to move rapidly relative to the magnet 246, which generates a rapid variation in the value of Sa calculated by the controller 66. To help illustrate this, trace T3 in FIG. 16 illustrates an example of a variation of the output from the sensor 248 as the head of the appliance 240 is moved across a creviced test surface TS2, whereas trace T4 illustrates the variation of the output received simultaneously from the reference sensor located on the internal surface of the stem 26. Trace T3 includes a series of troughs which each correspond with the entry of the nozzle 36 into a respective crevice in the test surface TS2.

As with the appliance 10, when the value of Sa falls below a first threshold value, which occurs when the tip of the nozzle 36 enters an interproximal gap, the controller 66 of the appliance 240 enters a second, or "primed", condition. With the tip of the nozzle 36 now located within the interproximal gap, the value of Sa increases rapidly. This can be to a value of approximately zero, or to a value greater than zero as the nozzle 36 moves away its distal position as the tip of the nozzle 36 begins to move over the adjacent tooth. When the value of Sa subsequently rises above a second threshold value, which is greater than the first threshold value, the controller 66 enters a third, or "ejection", condition in which the controller 66 operates the motor 50 to activate the pump 48 to eject the stored volume of water from the fluid outlet 62 of the pump 48 in the form of a burst of water. The burst of water passes through the second conduit 60 to be ejected from the fluid outlet 42 of the nozzle 36.

The invention claimed is:

1. A dental treatment appliance comprising:
   a handle;
   a datum component for engaging the teeth of a user, the datum component being moveable relative to the handle; and
   a dental treatment system comprising a contact member for engaging the teeth of the user, the contact member also being moveable relative to the handle, and a control circuit for actuating the treatment of the teeth of a user depending on relative movement between the contact member and the datum component as the appliance is moved along the teeth of a user, wherein the datum component comprises a sleeve that surrounds the contact member.

2. The appliance of claim 1, wherein the dental treatment system comprises a fluid delivery system for delivering a burst of working fluid to the teeth of a user.

3. The appliance of claim 2, wherein the contact member comprises a nozzle of the fluid delivery system.

4. The appliance of claim 1, wherein the control circuit is configured to detect relative movement between the contact member and the datum component as the appliance is moved along the teeth of a user, and to actuate the treatment of the teeth of the user depending on the detected relative movement.

5. The appliance of claim 1, wherein the control circuit comprises at least one sensor.

6. The appliance of claim 1, wherein the control circuit comprises a sensor for providing an output which varies with relative movement between the contact member and the datum component, and a controller for actuating the treatment of the teeth of the user depending on the output from the sensor.

7. The appliance of claim 6, wherein the sensor is connected to one of the contact member and the datum component.

8. The appliance of claim 7, wherein the sensor is mounted on said one of the contact member and the datum component.

9. The appliance of claim 7, comprising a component connected to the other one of the contact member and the datum component, and wherein the sensor is arranged to provide an output which varies with movement of the component relative thereto.

10. The appliance of claim 9, wherein the component is mounted on said other one of the contact member and the datum component.

11. The appliance of claim 9, wherein the component comprises a magnet.

12. The appliance of claim 11, wherein the sensor is a Hall effect sensor.

13. The appliance of claim 1, wherein the control circuit comprises a first sensor for providing an output which varies with movement of the contact member relative to the handle, a second sensor for providing an output which varies with movement of the datum component relative to the handle, and a controller for detecting relative movement between the contact member and the datum component from the outputs of the sensors, and for actuating the treatment of the teeth of the user depending on the detected relative movement.

14. The appliance of claim 13, comprising a first component connected to the contact member for movement therewith, and wherein the first sensor is arranged to provide an output which varies with movement of the first component relative to the handle, and a second component connected to the datum component for movement therewith, and wherein the second sensor is arranged to provide an output which varies with movement of the second component relative to the handle.

15. The appliance of claim 14, wherein the first component comprises a first magnet, and the second component comprises a second magnet.

16. The appliance of claim 15, wherein each of the first sensor and the second sensor is a Hall effect sensor.

17. The appliance of claim 14, comprising a first arm connected to the contact member for movement therewith, and wherein the first sensor is arranged to provide an output which varies with movement of the first arm relative to the handle, and a second arm connected to the datum component for movement therewith, and wherein the second sensor is arranged to provide an output which varies with movement of the second arm relative to the handle.

18. The appliance of claim 17, wherein the first arm and the second arm are mounted for pivoting movement relative to the handle about a common pivot axis.

19. The appliance of claim 1, wherein the contact member and the datum component are moveable relative to the handle in substantially the same direction.

20. The appliance of claim 1, wherein at least part of each of the contact member and the datum component is biased for movement relative to the handle in a direction which urges it against a user's teeth during use of the appliance.

21. The appliance of claim 20, wherein the contact member is biased in said direction by part of the dental treatment system.

22. The appliance of claim 21, wherein said part of the dental treatment system comprises a resilient fluid conduit.

23. The appliance of claim 21, wherein the datum component comprises at least one datum surface for engaging a user's teeth during use of the appliance.

24. The appliance of claim 23, wherein said at least one datum surface comprises a single, substantially planar, datum surface.

25. The appliance of claim 23, wherein said at least one datum surface comprises a plurality of datum surfaces.

26. The appliance of claim 25, wherein the plurality of datum surfaces are provided by a plurality of fingers of the datum component.

27. The appliance of claim 26, wherein the fingers are formed from resilient material.

28. The appliance of claim 23, comprising a resilient member for biasing the datum component in said direction.

29. The appliance of claim 28, wherein the resilient member is integral with said at least one datum surface.

30. The appliance of claim 1, wherein the contact member comprises a flange for engaging an inner surface of the sleeve to form a seal therewith.

* * * * *